(12) United States Patent
Mandal et al.

(10) Patent No.: US 7,811,817 B2
(45) Date of Patent: Oct. 12, 2010

(54) ESTABLISHMENT OF A HUMAN EMBRYONIC STEM CELL LINE USING MAMMALIAN CELLS

(75) Inventors: Arundhati Mandal, Navi Mumbai (IN); Shabari Tipnis, Navi Mumbai (IN); Geeta Ravindran, Navi Mumbai (IN); Jayant Kulkarni, Navi Mumbai (IN); Ameet Patki, Mumbai (IN); Rajarshi Pal, Navi Mumbai (IN); Bipasha Bose, Navi Mumbai (IN); Alam Firdos Kahn, Navi Mumbai (IN); Aparna Khanna, Navi Mumbai (IN)

(73) Assignee: Reliance Life Sciences Pvt. Ltd. (IN)

( * ) Notice: Subject to any disclaimer, the term of this patent is extended or adjusted under 35 U.S.C. 154(b) by 625 days.

(21) Appl. No.: 11/436,193

(22) Filed: May 17, 2006

(65) Prior Publication Data

US 2006/0286544 A1   Dec. 21, 2006

(30) Foreign Application Priority Data

May 17, 2005  (IN) .................... 595/MUM/2005

(51) Int. Cl.
*C12N 5/08* (2006.01)
*C12Q 1/00* (2006.01)
*A01N 63/00* (2006.01)

(52) U.S. Cl. .......................... 435/366; 435/4

(58) Field of Classification Search ........ None
See application file for complete search history.

(56) References Cited

U.S. PATENT DOCUMENTS

| 5,843,780 | A  | 12/1998 | Thomson |
| 6,200,806 | B1 | 3/2001  | Thomson |
| 2003/0073234 | A1 | 4/2003 | Amit et al. |
| 2003/0104616 | A1 | 6/2003 | Parikh et al. |
| 2005/0095702 | A1 | 5/2005 | Alam |
| 2006/0211109 | A1 | 9/2006 | Totey |

FOREIGN PATENT DOCUMENTS

WO   WO 03/018783   3/2003

OTHER PUBLICATIONS

Oh et al. Derivation and characterization of new human embryonic stem cell lines: SNUhES1, SNUhES2, and SNUhES3. Stem Cells 23:211-219, 2005.*
Bongso, A., et al., "Improved quality of human embryos when co-cultured with human ampullary cells," Human Reproduction, 4(6):706-713 (1989).
Brimble, S., et al., "Karyotypic Stability, Genotyping, Differentiation, Feeder-Free Maintenance, and Gene Expression Sampling in . . . ," Stem Cells Devel., 13:585-596 (2004).
Carpenter, M.K., "Feeder-free growth of undifferentiated human embryonic stem cells," Nature Biotechnology, 19(10):971-974 (2001).
Davila, J.C., et al., "Use and Application of Stem Cells in Toxicology," Toxicological Sciences, 79:214-223 (2004).
Doetschman, T.C., et al., "The in vitro development of blastocyst-derived embryonic stem cell lines: formation of visceral yolk . . . ," J. Embryol. exp. Morph., 87:27-45 (1985).
Evans, M.J., et al., "Derivation and Preliminary Characterization of Pluripotent Cell Lines from Porcine and Bovine Blastocysts," Theriogenology, 33:125-128 (1990).
Evans, M.J., and Kaufman, M.H., "Establishment in culture of pluripotential cells from mouse embryos," Nature 292:154-156 (1981).
Gardner, D.K., et al., "Culture and transfer of human blastocysts increases implantation rates and reduces the need for multiple embryo . . . ," Fert. Ster., 69(1):84-88 (1998).
Giles, J.R., et al., "Pluripotency of Cultured Rabbit Inner Cell Mass Cells Detected by Isozyme Analysis and Eye Pigmentation . . . ," Molecular Reprod. Devel., 36:130-138 (1993).
Graves, K. H., and Moreadith, R.W., "Derivation and Characterization of Putative Pluripotential Embryonic Stem Cells from . . . ," Molecular Reprod. Devel., 36:424-433 (1993).
Hamakazi, T., et al., "Hepatic maturation in differentiating embryonic stem cells in vitro," FEBS Letters 497:15-19 (2001).
Iannaccone, P.M., et al., "Pluripotent Embryonic Stem Cells from the Rat are Capable of Producing Chimeras," Developmental Biology, 163:288-292 (1994).
Itskovitz-Eldor, J., et al., "Differentiation of Human Embryonic Stem Cells into Embryoid Bodies Comprising the Three Embryonic Germ Layers," Molecular Med. 6(2):88-95 (2000).
Kulkarni, J.S., and Khanna, A., "Functional hepatocyte-like cells derived from mouse embryonic stem cells: A novel in vitro . . . " Toxicology in Vitro, 20:1014-1022 (2006).
Mandal, A., et al., "Characterization and in vitro differentiation potential of a new human embryonic stem cell line, ReliCell(R)hES1," Differentiation, 74:81-90 (2006).
Martin, G.R., "Isolation of a Pluripotent Cell Line from Early Mouse Embryos Cultured in Medium Conditioned by . . . ," Proc. Natl. Acad. Sci. USA 78(12):7634-7638 (1981).

(Continued)

*Primary Examiner*—Quang Nguyen
(74) *Attorney, Agent, or Firm*—Vinson & Elkins LLP

(57) ABSTRACT

Purified preparations of human embryonic stem cells with certain population-specific characteristics are disclosed. This preparation is characterized by the positive expression of the following pluripotent cell surface markers: SSEA-1 (−); SSEA-4 (+); TRA-1-60 (+); TRA-1-81 (+); alkaline phosphatase (+), as well as a set of ES cell markers including Oct-4, Nanog, Rex1, Sox2, Thy1, FGF4, ABCG2, Dppa5, UTF1, Cripto1, hTERT, Connexin-43 and Connexin-45. The cells of the preparation are negative for lineage specific markers like Keratin 8, Sox-1, NFH (ectoderm), MyoD, brachyury, cardiac-actin (mesoderm), HNF-3 beta, albumin, and PDX1 (endoderm). The cells of the preparation are human embryonic stem cells, have normal karyotypes, exhibit high telomerase activity and continue to proliferate in an undifferentiated state after continuous culture for over 40 passages. The embryonic stem cell line Relicell™ hES1 also retains the ability, throughout the culture, to differentiate into cell and tissue types derived from all three embryonic germ layers (endoderm, mesoderm and ectoderm). Methods for isolating a human embryonic stem cell line are also disclosed.

2 Claims, 14 Drawing Sheets

OTHER PUBLICATIONS

Mehra, N.K., et al., "Molecular diversity of HLA-A*02 in Asian Indians: predominance of A*0211," Tissue Antigens 57:502-507 (2001).

Meinecke-Tillman S., and Meinecke, B., "Isolation of ES-like cell lines from ovine and caprine preimplantation embryos," J. Anim. Breed. Genet. 113:413-426 (1996).

Notarianni, E., et al., "Derivation of pluripotent, embryonic cell lines from the pig and sheep," J. Reprod. Fert., Suppl. 43:255-260 (1991).

Notarianni, E., et al., "Maintenance and differentiation in culture of pluripotential embryonic cell lines from pig blastocysts," J. Reprod. Fert., Suppl. 41:51-56 (1990).

Reubinoff, B.E., et al., "Embryonic stem cell lines from human blastocysts: somatic differentiation in vitro," Nature Biotechnology 18:399-404 (2000).

Segev, H., et al., "Differentiation of Human Embryonic Stem Cells into Insulin-Producing Clusters," Stem Cells, 22:265-274 (2004).

Solter, D., and Knowles, B.B., "Immunosurgery of mouse blastocyst," Proc. Natl. Acad. Sci., 72(12):5099-5102 (1975).

Sukoyan, M.A., et al., "Isolation and Cultivation of Blastocyst-Derived Stem Cell Lines from American Mink (Mustela vison)," Mol. Reprod. Dev., 33:418-431 (1992).

Thomson, J.A., et al., "Embryonic Stem Cell Lines Derived from Human Blastocysts," Science, 282:1145-1147 (1998).

Thomson, J.A., and Marshall, V.S., "Primate Embryonic Stem Cells," Current Topics in Developmental Biology, 38:133-165 (1998).

Thomson, J.A., et al., "Pluripotent Cell Lines from Common Marmoset (*Callithrix jacchus*) Blastocysts," Biology of Reproduction 55:254-259 (1996).

Thomson, J.A., et al., "Isolation of a primate embryonic stem cell line," Proc. Natl. Acad. Sci. USA, 92:7844-7848 (1995).

PCT/IN2006/000169, International Search Report, Jan. 26, 2007.

Bok, H. et al., "Justice, Ethnicity, and Stem-Cell Banks," The Lancet, 364:118-121, 2004.

Bradley, J.A. et al., "Stem Cell Medicine Encounters the Immune System," Nature Reviews. Immunology, 2:859-871, 2002.

Josephson, Richard et al., "A Molecular Scheme for Improved Characterization of Human Embryonic Stem Cell Lines," BMC Biology, 4:28, 2006.

Lee, Jung Bok et al, "Available Human Feeder Cells for the Maintenance of Human Embryonic Stem Cells," Reproduction, 128:727-735, 2004.

* cited by examiner

ESTABLISHMENT OF A HUMAN EMBRYONIC STEM CELL LINE USING MAMMALIAN CELLS

CROSS-REFERENCES TO RELATED APPLICATIONS

This application claims priority to the provisional Indian Application No. 595/MUM/2005, filed May 7, 2005, and also claims priority to PCT application No. PCT/IN2006/00169, filed May 16, 2006.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present disclosure relates to the isolation, maintenance and propagation of human embryonic stem cells (hESC) from the inner cell mass of surplus embryos. This disclosure also relates to the characterization of isolated human ES cell lines, thereby demonstrating their in vitro differentiation potential and their prospective use in cell therapy and drug screening.

2. Description of Related Art

Pluripotent stem cells that are derived from the inner cell mass of a blastocyst are referred to as embryonic stem cells, while stem cells derived from primordial germ cells of the developing gonadal ridge are referred to as embryonic germ cells (Shamblott et al., (1998) Proc. Natl. Acad. Sci. U.S.A. 95(23):13726-31). Embryonic stem (ES) cells have been derived from the inner cell mass (ICM) of mammalian blastocysts (Evans and Kaufman, (1981) Nature, 292(5819):151-9; Martin, (1981) Proc. Natl. Acad. Sci. U.S.A., 78:7634-8). These cells are pluripotent, and are capable of developing into any organ or tissue type. ES cells are capable of proliferating in vitro in an undifferentiated state, maintaining a normal karyotype through prolonged culture, and maintaining the potential to differentiate into derivatives of all three embryonic germ layers (i.e., mesoderm, ectoderm and endoderm) (Itskovitz-Eldor et al., (2000) Mol. Med., 6(2):88-95).

ES cells represent a powerful model system for the investigation of mechanisms underlying pluripotent cell biology and differentiation within the early embryo, as well as providing opportunities for genetic manipulation. Appropriate proliferation and differentiation of ES cells can be used to generate an unlimited source of cells, suitable for cell-based therapies of diseases that result from cell damage or dysfunction.

ES cells have been isolated from the ICM of blastocyst-stage embryos in mice (Solter and Knowles, (1975) 72(12):5099-5102), as well as several other species. For example, pluripotent cell lines have also been derived from pre-implantation embryos of several domestic and laboratory animal species, such as bovine (Evans et al., (1990), Theriogenology, 33:125-8), porcine (Evans et al., (1990) supra; Notarianni et al., (1990) J. Reprod. Fertil. Suppl., 41:51-6), sheep and goat (Meinecke-Tillmann and Meinecke, (1996), J. Animal Breeding and Genetics, 113:413-26; Notarianni, et al., (1991), J. Reprod. Fertil. Suppl., 43:255-60) rabbit (Giles et al., (1993) Mol. Reprod. Dev., 36(2):130-8; Graves et al., (1993) Mol. Reprod. and Dev., 36:424-33), mink (Sukoyan et al., (1992), Mol. Reprod. and Dev., 33:418-31), rat (Iannaccona et al., (1994), Dev. Biology, 163:288-92), hamster (Doetschman et al., (1985) J. Embryol. Exp. Morphol., 87:27-45), and rhesus and marmoset monkeys (Thomson et al., (1995) Proc. Natl. Acad. Sci. 92(17):7844-8; and Thomson, et al., (1996), Biol. Reprod., 55:254-59). Thomson et al. (1998) Science 282 (5391):1145-7 and Reubinoff et al. (2000) Nat. Biotech. 18(5):559) have reported the derivation of human ES cell lines.

Early work on ES cells was done in mice (Doetschman et al., (1985) J. Embr. Exp. Morphol., 87:27-45). Mouse ES cells are undifferentiated pluripotent cells derived in vitro from preimplantation embryos, and maintain an undifferentiated state through serial passages when cultured in the presence of fibroblast feeder layers and leukemia inhibitory factor (LIF). Although research with mouse ES cells facilitates the understanding of developmental processes and genetic diseases, significant differences in human and mouse development limit the use of mouse ES cells as a model of human development. The morphology, cell surface markers and growth requirements of ES cells derived from other species are significantly different than for mouse ES cells. Further, mouse and human embryos differ significantly in temporal expression of embryonic genes, such as in the formation of the egg cylinder versus the embryonic disc (Kaufman, The Atlas of Mouse Development; London; Academic Press, 1992), in the proposed derivation of some early lineages (O'Rahilly and Muller; Developmental stages in Human Embryos, Washington; Carnegie Institution of Washington, 1987), in the structure and function of the extraembryonic membranes and placenta (Mossman, Vertebrate Fetal membranes; New Brunswick; Rutgers, 1987), in growth factor requirements for development (e.g., the hematopoietic system-Lapidot Lab. Animal Sciences 1994), and in adult structure and function (e.g., central nervous system). To overcome these differences and to have a better insight into human embryonic development, ES cells were successfully established from primates (Thomson et al., 1995 and 1998, supra).

The cell lines currently available that most closely resemble human ES cells are human embryonic carcinoma (EC) cells, which are pluripotent, immortal cells derived from teratocarcinomas (Andrews et al., (1984) Lab. Invest. 50(2): 147-162; Andrews et al., in: Robertson E., ed. Teratocarcinomas and Embryonic Stem Cells: A Practical Approach. Oxford: IRL press, pp. 207-246, 1987). EC cells can be induced to differentiate in culture, and the differentiation is characterized by the loss of specific cell surface markers (SSEA-3, SSEA-4, TRA-1-60, and TRA-1-81) and the appearance of new markers (Andrews et al., (1987), supra). Human EC cells will form teratocarcinomas in nude mice with derivatives of multiple embryonic lineages in the tumors. Similar mouse EC cell lines have been derived from teratocarcinomas, and, in general, their developmental potential is much more limited than mouse ES cells (Rossant and Papaioannou, (1984) Cell Differ. 15:155-161). Teratocarcinomas are tumors derived from germ cells, and although germ cells (like ES cells) are theoretically totipotent (i.e., capable of forming all cell types in the body), the more limited developmental potential and the abnormal karyotypes of EC cells are thought to result from selective pressures in the teratocarcinoma tumor environment (Rossant and Papaioannou, (1984), supra). ES cells, on the other hand, are thought to retain greater developmental potential because they are derived from normal ES in vitro, without the selective pressures of the teratocarcinoma environment.

The first human pluripotent ES cell line was published in 1998 (Thomson et al., (1998), supra). A few years later, human embryonic stem cell lines ("human ES cell lines") were established from human blastocysts (Reubinoff et al., (2000), supra). To date, the majority of described human ES cell lines have been derived from day 5 to day 8 blastocysts produced for clinical purposes after in vitro fertilization (IVF) or intracytoplasmic sperm injection (ICSI). In addition, the isolation of ICM from the morula (day 4 embryo) stage has also been reported (Giles et al., 1993).

Human ES cells can be isolated from human blastocysts. Human blastocysts can be obtained from human in vivo pre-implantation embryos or from IVF embryos, intracytoplasmic sperm injection, ooplasm transfer, or other methods well known to those of skill in the art. Human ES cells may be derived from a blastocyst using standard immunosurgery techniques as disclosed in U.S. Pat. Nos. 5,843,780 and 6,200,806, Thomson et al., (1998), supra, and Reubinoff et al., (2000), supra (each incorporated herein by reference), whole embryo-culture method, or by a unique method of laser ablation (U.S. Ser. No. 10/226,711, incorporated herein by reference). Alternatively, a single cell human embryo can be expanded to the blastocyst stage. Although numerous human ES cell lines have been derived to date, only a few of them are well characterized in terms of their unique identity, self-renewal capacity and differentiation potential (Brimble et al., (2004) Stem Cells Dev., 13:585-7).

One method well known to those of skill in the art for generating human ES cells is by immunosurgery. This method involves removing the zona-pellucida from the blastocyst and isolating the ICM by immunosurgery, in which the trophectoderm cells are lysed and removed from the intact ICM by gentle pipetting. The ICM is then plated in a tissue culture flask containing the appropriate medium, which enables its outgrowth. After 9 to 15 days, the ICM derived outgrowth is dissociated into clumps either by a mechanical dissociation or by enzymatic degradation, and the cells are re-plated in a fresh tissue culture medium. Colonies demonstrating undifferentiated morphology are individually selected by micropipette, mechanically dissociated into clumps, and re-plated. Resulting ES cells are then routinely split every 1-2 weeks to maintain the cells in a generally undifferentiated state. For a more detailed description of the immunosurgery technique, see U.S. Pat. No. 5,843,780; Thomson et al., (1998), supra; Thomson et al., (1998) Curr. Top. Dev. Biol. 38:133; Thomson et al., (1995), supra; Bongso et al., (1989) Hum. Reprod. 4(6):706-13; Gardner et al., (1998), Fert. and Sterility, 69(1):84-8), each of which is incorporated herein by reference.

Methods of maintaining human ES cells in an undifferentiated pluripotent state include but are not limited to culturing the cells in the presence of a feeder layer, under feeder-free conditions, in the presence of conditioned medium, and/or on an extra-cellular matrix supplemented with serum or conditioned medium. The feeder layers may be, for example, γ-irradiated or mitomycin-C treated mouse embryonic fibroblast (MEF) cells or human fibroblast cells. When cultured in a standard culture environment in the absence of a feeder layer, human ES cells may rapidly differentiate or fail to survive. Unlike murine ES cells, the presence of exogenously added LIF does not prevent differentiation of human ES cells. Feeder cell layers are used to provide a microenvironment (or niche) to prevent stem cells from differentiating along their natural course. These feeder layers appear to provide the stem cells with external signals such as secretion of factors and cell-to-cell interactions mediated by integral membrane proteins. Watt and Hogan, (2000) Science 287(5457):1427-30.

In light of the fact that secretion factors and direct cell-to-cell interactions control in vitro survival, proliferation, and differentiation of the stem cells, an ideal environment should consist of healthy feeder tissues with normal microstructures and functions, or simulate such an environment. Examples of feeder cells include but are not limited to: (1) irradiation-inactivated mouse embryonic fibroblasts; (2) mitotically (mitomycin C) inactivated mouse embryonic fibroblasts; and (3) irradiation-inactivated STO fibroblast feeder layers. See Thomson et al., (1998) supra; Reubinoff et al. (2000), supra; and Shamblott et al., (1998) Proc. Natl. Acad. Sci. U.S.A. 95(23): 13726-31, each incorporated herein by reference.

In spite of the progress in effectively culturing ES cells, several significant disadvantages with these methods still exist. For example, exposure to animal pathogens through MEF-conditioned medium or matrigel matrix is still a possibility. The major obstacle of the use of human ES cells in human therapy is that the originally described methods to propagate human ES cells involve culturing the human ES cells on a layer of feeder cells of non-human origin, and in the presence of nutrient serum of non-human origin. More recently, extensive research into improving culture systems for human ES cells has concentrated on the ability to grow ES cells under serum free/feeder-free conditions. For example, to ensure a feeder-free environment for the growth of human ES cells, a substitute system based on medium supplemented with serum replacement (SR), transforming growth factor β1 (TGF-β1), LIF, bFGF and a fibronectin matrix has also been tried (Amit et al (2004), Biol. Reprod. 70(3):837-45). Evaluation of methods for derivation and propagation of undifferentiated human ES cells on human feeders or feeder-free matrices continues.

Detailed characterization of human ES cells may include analysis at the cellular and molecular level, as well as an analysis of the regulation of cell cycle, expression of high telomerase activity, genetic stability, particular HLA and STR types, and differentiation potential under in vitro and in vivo conditions. The profile of surface antigens displayed in undifferentiated human ES cells matches that of human ES cells and human EC cells. Undifferentiated human ES express globo-series cell surface markers such as stage specific embryonic antigens (SSEAs), for example SSEA-3 and SSEA-4, as well as tumor recognition antigens, for example TRA-1-60 and TRA-1-81. In addition, human ES cells express POU5F1, promoter-encoded transcription factor OCT-4, E-cadherin and the gap junction protein connexin-43 (Andrews et al., 2002). Unlike mouse ES cells, undifferentiated human ES cells do not express SSEA-1. Undifferentiated human ES cells stain positively for alkaline phosphatase, and demonstrate high telomerase activity indicative of their increased capacity for self-renewal.

The genetic stability of human ES cells can be assessed by using the standard G-banding technique, which is well-known to a person of ordinary skill in the art. Normally human ES cells maintain a stable karyotype, either 46 XX or 46 XY, even after prolonged continuous culture. With increased passaging, however, the cells tend to show abnormal karyotypes including trisomies of chromosomes 12-17 and the X chromosome. The unlimited proliferative potential of ES cells is directly correlated with telomerase activity. A Telomerase Repeat Amplification Protocol (TRAP) assay may be performed to assess telomerase activity in a particular ES cell line. The assay may be performed either using a radioisotopic method (Thomson et al., (1998), supra, or a non-radioisotopic method (Oh et al., (2004) Stem Cells 23(2): 211-19).

Human ES cells have the potential to differentiate into all cell types of the human body. The developmental potential of these cells after prolonged culture may be examined in vitro through the formation of embryoid bodies and in vivo through the formation of teratomas in SCID mice (Evans and Kaufman, (1983), supra). To confirm that human ES cells retain their in vitro differentiation capacity, embryoid bodies can be formed in suspension culture and analyzed by RT-PCR and immunocytochemistry for markers representing each of the three germ layers (Itskovitz-Eldor, (2000), supra, and Shamblott et al., (1998), supra).

Human ES cells offer insight into developmental events, which cannot be studied in explant systems. Screens based on the in vitro differentiation of human ES cells to specific lineages can identify gene targets, which can be used to design or reprogram tissue generation or regeneration, as well as identify teratogenic or toxic compounds. Replacement of non-functional cells, tissues, or organs using ES cell technology may offer a therapeutic treatment in the case of degenerative diseases like Parkinsons disease, stroke, cardiac ischemia, hepatic failure, juvenile-onset diabetes mellitus, or other diseases or conditions that result from the death or dysfunction of one or several cell types (Wobus and Boheler, (2005), Physiol. Rev. 85(2):635-8). Nevertheless, in order for the potential therapeutic applications of human ES cell technology to become reality, techniques must enable the production of enriched human ES-cell-derived specialized cell types under defined growth conditions, a pathogen-free environment, and survival under extended in vitro conditions.

At present, there are a limited number of human ES cell lines available and they represent a very small sample of the genetic diversity of the human population. Hence, there is an urgent need for the generation and characterization of additional cell lines, as each cell line may have its own set of characteristics and advantages for different applications in a particular population. Furthermore, the availability of more human ES cell lines for comparison will facilitate the global efforts to define the criteria of human ES cells and the establishment of appropriate and robust methods for the maintenance and expansion of human ES cells.

BRIEF SUMMARY OF THE INVENTION

The present disclosure is directed to the isolation and identification of pluripotent human embryonic stem (ES) cells with certain genetic characteristics that will allow the human ES cells to be more effectively utilized to the advantage of a particular population, for example the Indian population. Preferably, the human ES cells will have human leukocyte antigen (HLA) alleles which express HLAs that are generally compatible with a significant percentage of the target population. While certain of the HLAs identified may be expressed by less than half of those in the target population, this frequency is still considered significant, since therapeutic treatments generated from the ES cell lines which express compatible HLAs are more likely to be effective in that subset of the target population.

An embodiment of the present disclosure is directed to a purified preparation of pluripotent human ES cells, wherein the cells comprise:
  (i) the ability to differentiate to derivatives of endoderm, mesoderm, and ectoderm tissues,
  (ii) a normal karyotype,
  (iii) the ability to propagate in an in vitro culture for at least about 25 passages, and
  (iv) one or more of the HLA alleles set forth in Table 4.

The term "purified preparation of pluripotent human ES cells" as used herein means that substantially all of the human ES cells in the purified preparation have the recited characteristics. Therefore, a purified preparation of pluripotent human ES cells may comprise cells wherein at least about 50%, 55%, 60%, 65%, 70%, 75%, 80%, 85%, 90%, 95%, or 99% have the characteristics of the general population of the human ES cells in the preparation, such as, for example, the ability to differentiate to derivatives of endoderm, mesoderm, and ectoderm tissues, a normal karyotype, the ability to propagate in an in vitro culture for at least about 25 passages, and one or more of the HLA alleles set forth in Table 4.

The preparation of pluripotent human ES cells may further comprise any number of the HLA alleles set forth in Table 4. Preferably, the cells comprise the entire HLA profile set forth in Table 4. The human ES cells of the present disclosure preferably have one or more of the additional characteristics that have been identified with human ES cells. For example, the human ES cells of the present disclosure (1) may proliferate in an in vitro culture for over one year; (2) are inhibited from differentiating when cultured on a fibroblast feeder layer (e.g., an embryonic fibroblast feeder layer, or a mouse or human fibroblast feeder layer), under feeder-free conditions, or in the presence of conditioned medium; (3) are positive for the SSEA-3 and SSEA-4 markers; (4) are positive for the TRA-1-60, and TRA-1-81 markers; (5) express alkaline phosphatase; (6) express high levels of telomerase; or (7) are capable of forming embryoid bodies when placed in suspension culture. Preferably, the preparations of pluripotent human ES cells of the present disclosure have not been exposed to animal generated antibodies and sera.

In preferred embodiments, the preparation remains substantially undifferentiated after about 40 passages in culture, more preferably after about 60 passages in culture, and most preferably after about 100 passages in culture. Although colonies of undifferentiated ES cells within the preparation may be adjacent to neighboring cells that are differentiated, the preparation will nevertheless remain substantially undifferentiated when the preparation is cultured or passaged under appropriate conditions, and individual undifferentiated ES cells constitute a substantial proportion of the cell population. Preparations that are substantially undifferentiated contain at least about 20% undifferentiated ES cells, and may contain at least about 40%, 50%, 60%, 70%, 80%, or 90% ES cells. In another preferred embodiment, the human ES cells of the present disclosure further comprise one or more of the short tandem repeat (STR) loci set forth in Table 5, and may comprise any number, including all, of the STR loci set forth in Table 5.

Another embodiment of the present disclosure is directed to a method of screening a substance for its effect on the purified preparation of pluripotent human embryonic stem cells of claim 1, comprising:
  a) obtaining the purified preparation of pluripotent human embryonic stem cells;
  b) combining the preparation with the substance; and
  c) determining any effect of the substance on the cells in the preparation.

The substance tested may be such as small molecule drugs, peptides, polynucleotides, and the like. In certain embodiments, determining any effect of the substance on the cells in the preparation comprises (1) determining whether the substance affects the growth of the cells in the preparation; (2) determining whether the substance affects differentiation of the cells in the preparation; (3) determining whether the substance affects expression of a marker or receptor by the cells in the preparation; (4) determining whether the substance is toxic to the cells in the preparation; or (5) determining any phenotypic or metabolic changes to the cells in the preparation. In any of the methods disclosed above, the purified preparation of pluripotent human embryonic stem cells may be differentiated prior to combining the preparation with the substance, for example by exposing the preparation to culture conditions that promote differentiation toward a particular cell lineage or cell type. The cell lineage or cell type may be any that are well known to those of skill in the art including, without limitation, neuronal cells, glial cells, neurons, neuroprogenitor cells, hepatocytes, cardiomyocytes, pancreatic islet cells, or any other cellular types that may be derived from human ES cells.

Another embodiment of the present disclosure is directed to methods of selecting a pluripotent human ES cell line that will provide improved HLA matching for individuals in a particular population of interest, for example the Indian population, by screening human ES cells for expression of certain HLA alleles that commonly found in the population of interest. HLA alleles are commonly found in the population of interest if they are present in at least about 10%, 20%, 30%, 40%, 50%, 60%, 70%, 80%, 90%, or 95% of individuals in the population of interest. The population of interest may be based on nationality, ethnicity, or genetic characteristics of a particular group of individuals. Those of skill in the art are aware of HLA alleles that are commonly found in various populations of interest. Potential transplantation therapies with cells, tissues or organs derived from human ES cells will be governed by typical HLA matching criteria, for example potential recipients will have to be matched for suitable HLA loci with the donor human ES cell line. Therefore, the identification of such human ES cell lines has great potential value for therapeutic treatments.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

MEF (Heat inactivated); Lane 5: ReliCell™ hES1 (p37); Lane 6: ReliCell™ hES1 (p37, Heat inactivated); Lane 7: Internal control; Lane 8: TSR8 control template (1.5 µl, provided with the kit).

Figure 9:
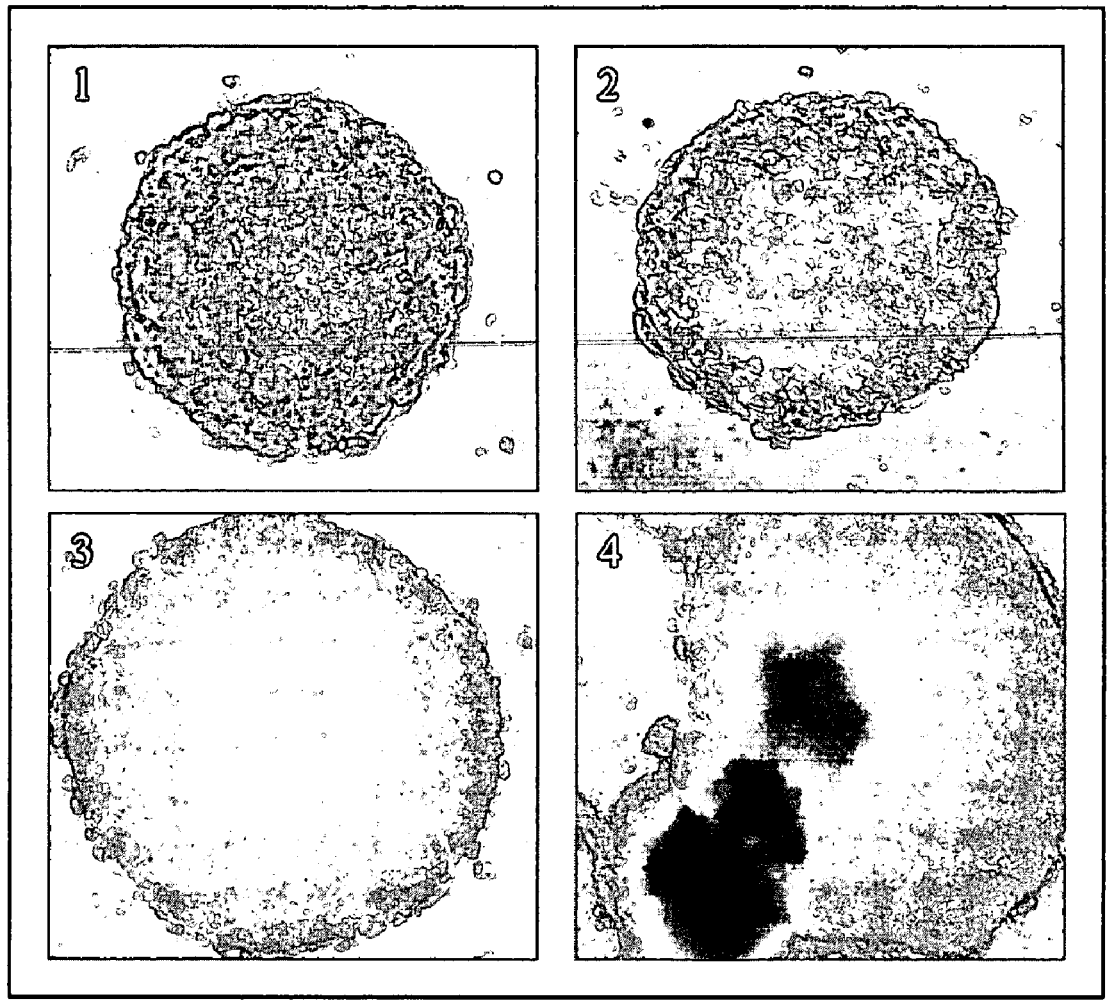

FIG. 9 shows four photographs of embryoid bodies at increasing days in suspension culture maintained in a suitable medium (w/o hLIF) to induce differentiation in vitro. Photograph 8.1 shows a loose aggregate/colony of human ES cells after 6 days in suspension culture; Photograph 8.2 shows a compact embryoid body at day 10; Photograph 8.3 demonstrates the initiation of blood island formation at day 14; and Photograph 8.4 shows dense formation of blood islands at day 21, which is the evidence of angiogenesis in vitro.

Figure 10:
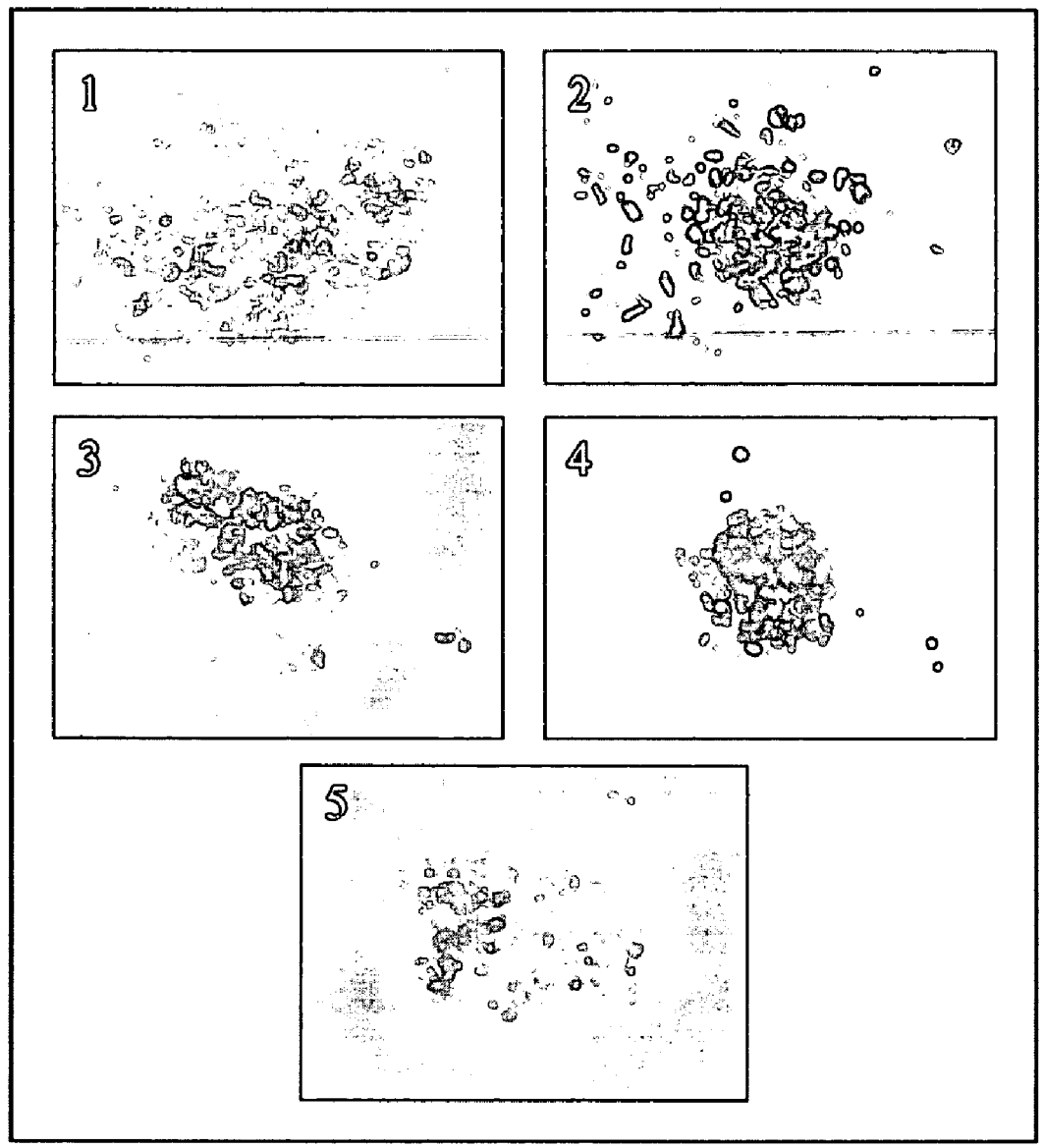

FIG. 10 shows photomicrographs demonstrating the in vitro differentiation potential of the Relicell™ hES1 cell line by immunochemistry of fixed embryoid bodies (day 14) in 2-well chamber slides. Photograph 10.1 shows nestin (+) immunostaining (ectoderm); Photographs 10.2 and 10.3 show smooth muscle actin and brachyury (+) immunostaining respectively (mesoderm), and Photographs 10.4 and 10.5 show AFP and GATA-4 (+) immunostaining respectively (endoderm), thereby confirming the RT-PCR results. All antibodies used for the study were FITC-conjugated. Pictures were acquired using a Nikon E600 inverted microscope.

Figure 11:
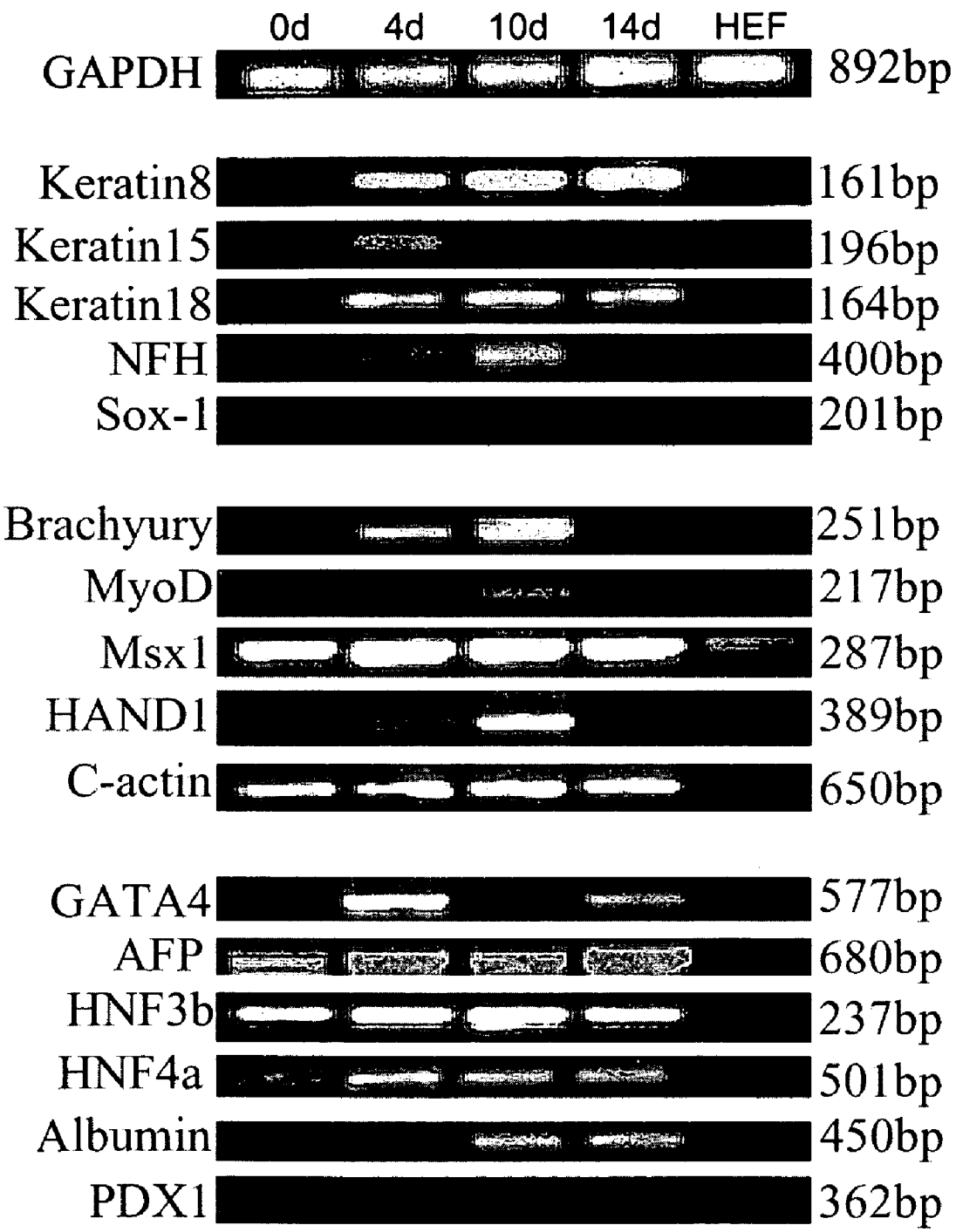

FIG. 11 shows the differential gene expression of a set of lineage-specific markers indicative of cells derived from the three germ layers present in embryoid bodies (passage 32) generated from Relicell™ human ES1 cell line, including: (1) Keratin 8, Keratin 15, Keratin 18, NFH, Sox-1 (ectoderm); (2) Brachyury, MyoD, Msx1, HAND1, cardiac actin (mesoderm); and (3) GATA-4, AFP, HNF-3b, HNF-4a, albumin, and PDX1 (endoderm). The photograph demonstrates high mRNA levels of the aforesaid markers from day 10 to day 14 of embryoid body formation, thereby indicating in vitro differentiation potential of the human ES cell line into all three lineages. HEF cells were used as a negative control, and GAPDH was used as a housekeeping gene control.

Figure 12:
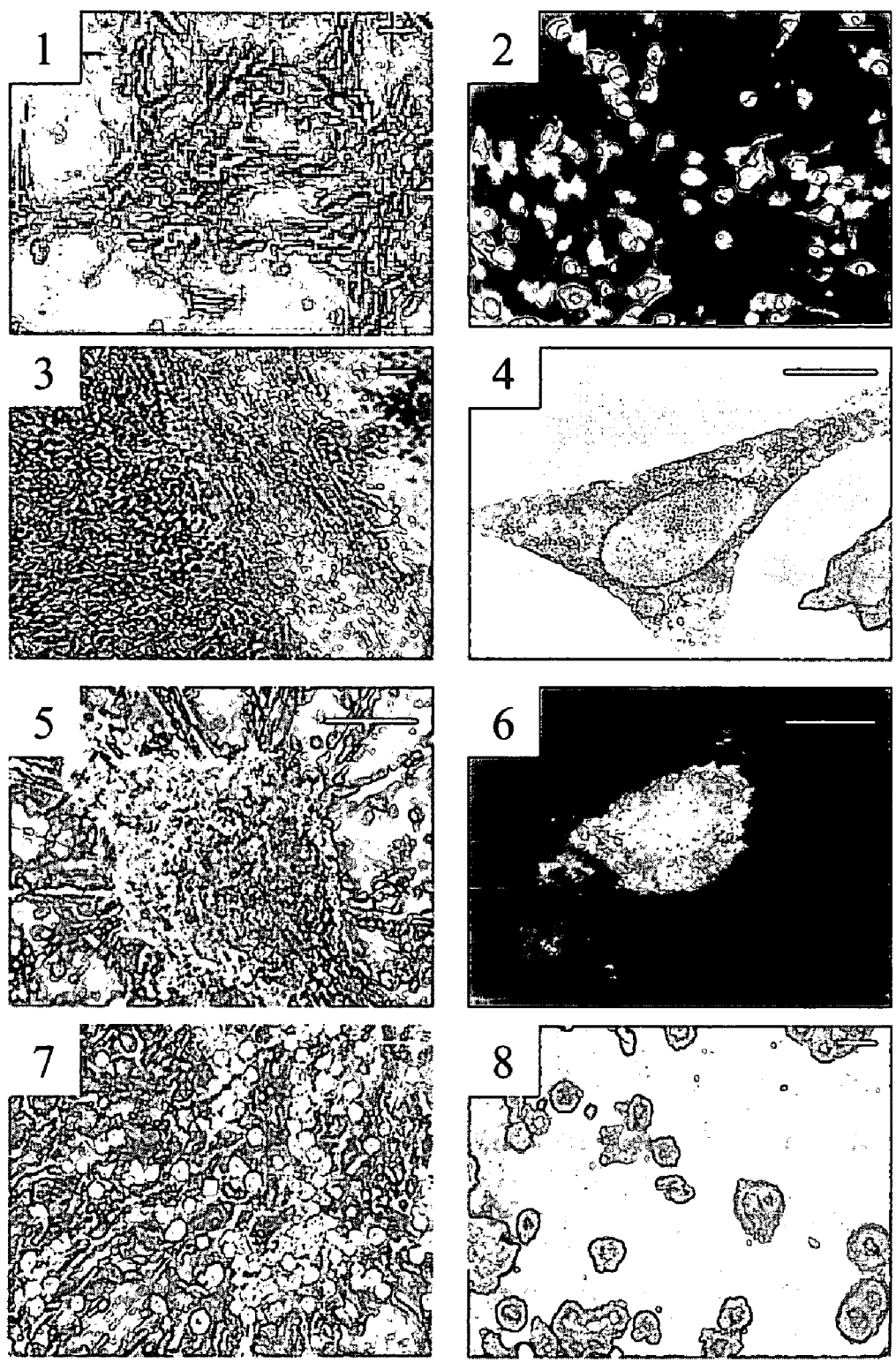

FIG. 12 shows an evaluation of the in vitro differentiation potential of Relicell™ hES1. Phase contrast micrographs of examples of cells of different phenotypes differentiated under suitable in vitro conditions from undifferentiated human ES cells through embryoid bodies formation as follows: Panel A: neurons with multiple processes; Panel C: cardiomyocytes; Panel E: pancreatic-islet; and Panel G: oval shaped hepatoblasts. In addition, immunostaining of these differentiated cells was performed with certain cell specific markers: Panel B: MAP-2; Panel D: cardiac troponin-I; Panel F: PDX-1; and Panel H: CK18.

Figure 13:
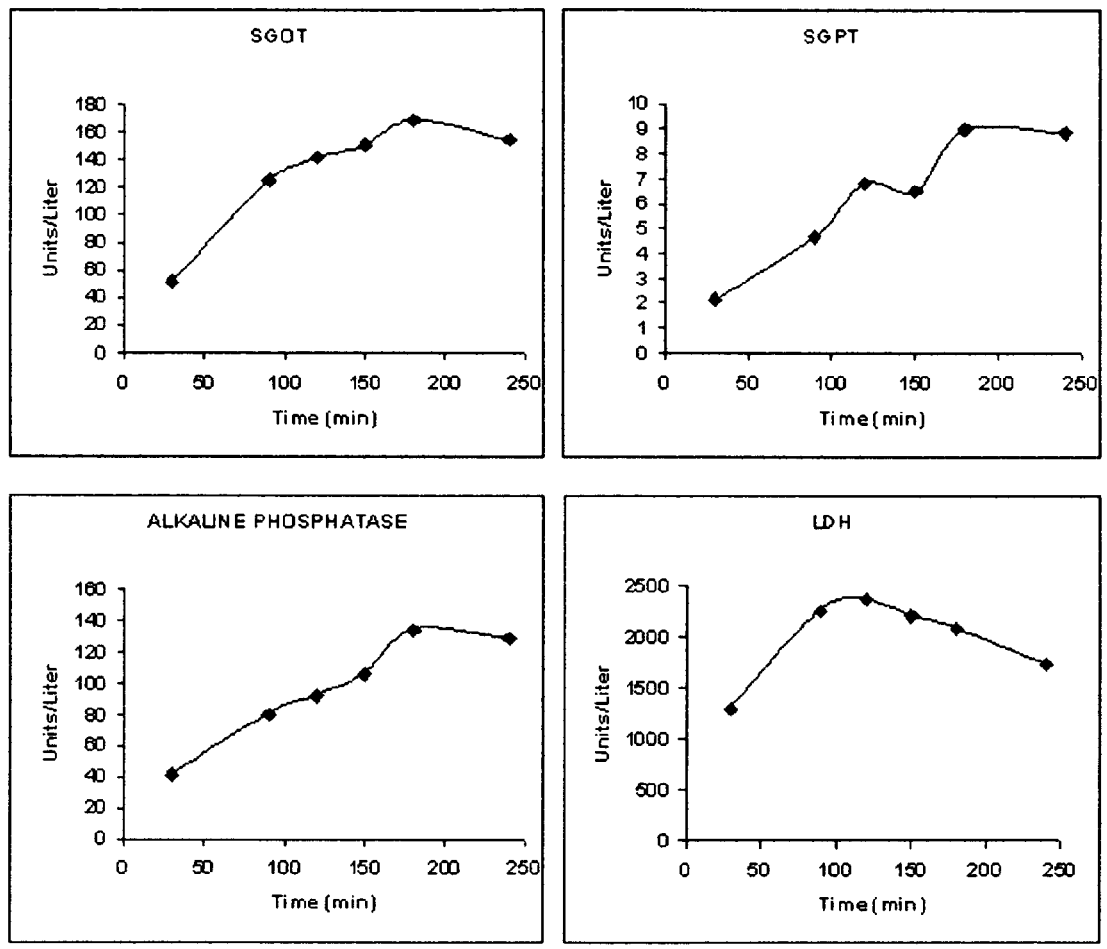

FIG. 13 shows a graphical representation of the exposure of HepG2, a hepatocarcinoma cell line, to carbon tetrachloride (0.6%) for various time intervals. In addition, levels of the following enzymes were determined by biochemical methods: Panel A: serum glutamate oxalo-acetate aminotransferase (SGOT); Panel B: serum glutamate pyruvate aminotransferase (SGPT); Panel C: alkaline phosphatase (ALP); and Panel D: lactate dehydrogenase (LDH).

Figure 14:
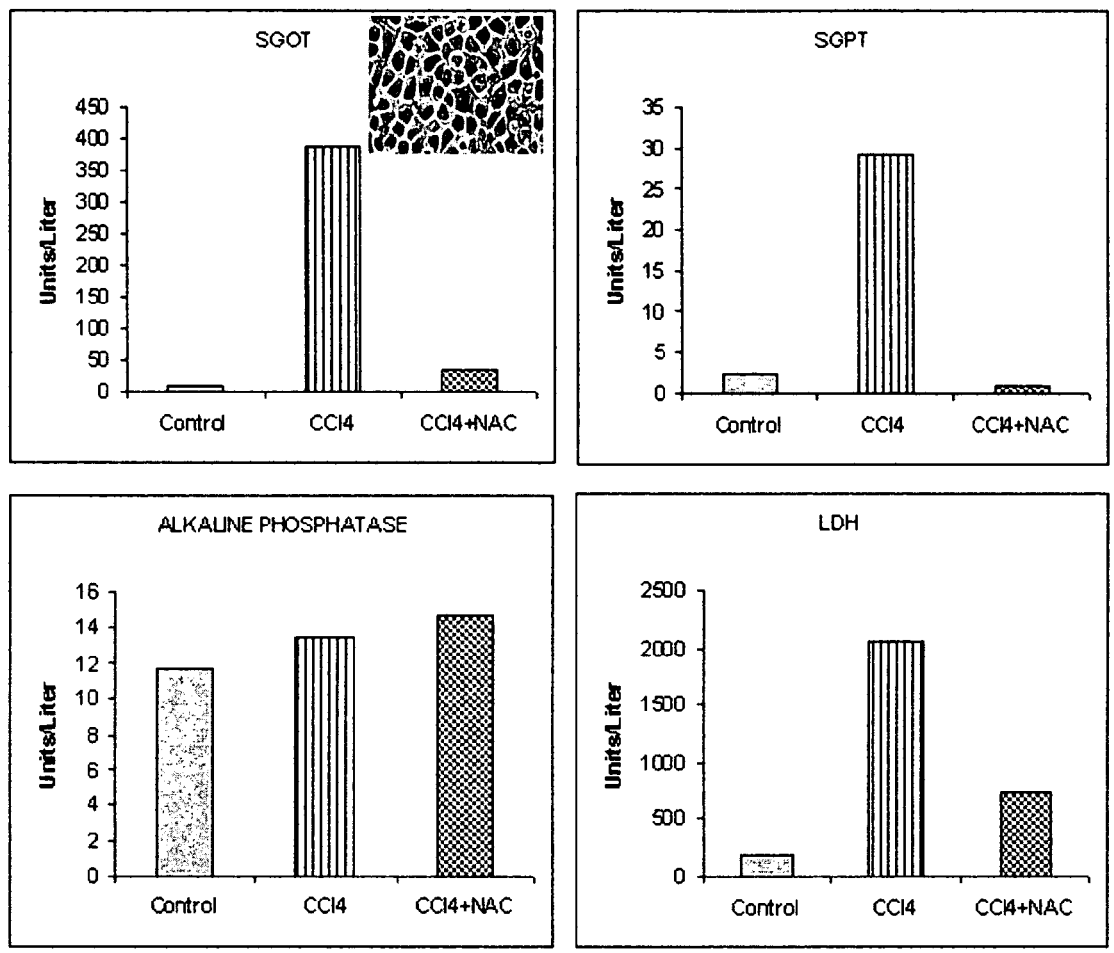

FIG. 14 shows the establishment of mouse ES cell-derived hepatocytes as an in vitro hepatotoxicity model. Hepatocytes were differentiated from mouse ES cells and exposed to carbon tetrachloride (0.6%) for 180 minutes in the absence and presence of N-acetylcysteine (NAC), an antioxidant (25 µM). Levels of the following enzymes were determined by biochemical methods: Panel A: SGOT; Panel B: SGPT; Panel C: ALP; and Panel D: LDH.

DETAILED DESCRIPTION OF THE INVENTION

The present disclosure is directed to the establishment of well-characterized human ES cell lines in terms of their unique identity, self renewal capacity and differentiation potential. In particular, human ES cell lines are generated which have properties that are well-suited for generating therapeutic treatments for a specific population of recipients. This population may be based on nationality, ethnicity, or genetic characteristics of a particular group of individuals. Such human ES cell lines may offer characteristics and advantages to that particular population for various applications such as cell replacement therapy, drug screening, and functional genomics. The human ES cells may be identified as having certain advantages for treating a particular population identified by certain genetic properties, such as the presence of certain major histocompatibility complex (MHC) alleles, human leukocyte antigens (HLA), or short tandem repeat (STR) identifiers, which are prevalent in the population of interest. Isolating human ES cells with one or more common genetic properties with the general population increases the likelihood that these ES cells can be used to develop therapeutic applications or other information that will generally benefit that population. For example, the more histocompatible the human ES cells are with the general population of interest, the more likely that the ES cells can be used to generate therapeutic treatments for that population. In particularly preferred embodiments, the population of interest is the Indian population.

The MHC is a region of the chromosome containing HLA or MRC genes, which are divided into three categories: class I, class II and class III. In humans, the MHC class I genes include HLA-A, HLA-B and HLA-C, while the MHC class II genes include HLA-DP, HLA-DQ and HLA-DR (Golub and Green, (1991), Immunology: A Synthesis, Second Edition, Chapter 15). MHC class I and class II molecules bind peptide fragments of self- or foreign-antigens, and are inspected on the cell surface by T lymphocytes. Thus, these molecules can stimulate cellular or humoral immune attack (Germain, (1994), Cell 76:287-299). Complete product lines are commercially available for typing all classical HLA loci including A, B, C, DRA, DRB1, DRB3, DRB4, DRB5, DQA1, DQB1, DPA1, and DPB1. By identifying ES cell lines with genetic factors such as, for example, HLA alleles, which are more prevalent in the general population, the cell lines can be used to derive therapeutic treatments that will be more effective in the target population. For example, a preferred embodiment of the present disclosure is directed to generating human ES cell lines that have a higher percentage of markers, such as immunogenetic markers, in common with the Indian population than a randomly isolated human ES cell line. This will reduce the risk of immune rejection of therapeutic treatments derived from the ES cells in the population.

For example, studies of the genetic diversity of HLA isotypes in the North Indian population have revealed a high occurrence of certain HLA alleles in that population. In one such study, Mehra et al., (2001) Tissue Antigens 57(6):502-7, observed an unexpectedly low frequency of HLA-A*0201 (3.8%) in Asian Indians, in contrast to its distribution in Western Caucasions in whom it constitutes 95% of the HLA-A2 repertoire. This example signals the importance of identifying human ES cell lines that are generally histocompatible with the patient population of interest.

Human ES cells of the present disclosure are particularly advantageous due to several unique properties of these cells, which generally:

(1) Are capable of differentiating into a variety of tissue types, belonging to all three germ layers (endoderm, ectoderm, and mesoderm);

(2) Are self-renewing and capable of propagating in culture for at least about 40 to about 100 passages or more while maintaining pluripotency, high telomerase activity, and normal karyotype;

(3) Are capable of forming embryoid bodies (EBs);

(4) Possess one or more unique HLA alleles, which will provide better matching to recipients during transplantation for a selected population of patients, for example an Indian population;

(5) Possess one or more unique short tandem repeat (STR) loci, which will provide better matching to recipients during transplantation for a selected population of patients, for example an Indian population;

(6) Can be used to screen compounds, for example small molecules and drugs, for their effect on the cell population, cell toxicity, or modulation of gene or protein expression; and (7) Can be used as an alternative to conventional in vitro toxicity models for drug metabolism and toxicity studies, using, for example, hepatocytes, cardiomyocytes, neurons, pancreatic islet cells, or other cellular types derived from human ES cells of the present disclosure.

A particularly preferred human ES cell line, which is described herein, is the Relicell ™ hES1 cell line (Mandal et al., (2006) Differentiation 74:81-90, incorporated herein by reference). This cell line has been deposited with the National Center for Cell Sciences (NCCS), Pune, India, and was deposited with American Type Culture Collection (ATCC) on Jan. 24, 2007, and assigned Patent Deposit Designation No. PTA-8172. This cell line expresses high levels of cell surface markers such as SSEA-3, SSEA-4, TRA-1-60, and TRA-1-81, the transcription factor Oct-4, alkaline phosphatase, and telomerase. This cell line retains normal karyotype in long-term culture and has a distinct identity as revealed by DNA fingerprinting by STR analysis. Examination of the in vitro differentiation potential of this cell line demonstrated that it is capable of giving rise to dopaminergic neurons, cardiomyocytes, pancreatic islets, and hepatocyte-like cells belonging to ectoderm, mesoderm, and endoderm lineages, respectively.

Human ES cells of the present disclosure are generated from the ICM of the blastocyst stage of a mammalian embryo. In preferred embodiments, the pluripotent human ES cells are capable of self-regeneration and can give rise to cells of all three lineages (ectoderm, mesoderm and endoderm). As used herein, the phrase "pluripotent human ES cells" refers to cells that are derived from the ICM of the blastocyst stage of a mammalian embryo. Pluripotent cells are capable of self-regeneration and differentiation to cells of all three lineages. As used herein the term "differentiation" refers to a process whereby undifferentiated ES cells acquire a state where cells are more specialized and have characteristics of special tissues. These special tissues show the expression of tissue-specific markers at the cellular and molecular levels. The differentiation potential of an ES cell line is the capacity of the cell line to give rise to cell types belonging to all three germ layers (ectoderm, mesoderm and endoderm, including teratocarcinomas). The in vitro differentiation potential of ES cells can be demonstrated by culturing the cells under conditions suitable for differentiation. In addition, the in vivo differentiation potential of ES cells can be shown by injecting the cells into SCID mice to form teratomas.

The pluripotent ES cells of the present disclosure are lineage uncommitted (i.e., they are not committed to a particular germ lineage such as ectoderm, mesoderm and endoderm). Pluripotent human ES cells may also have a high self-renewal capacity and possess differentiation potential, both in vitro and in vivo, or can remain dormant or quiescent within a cell, tissue, or organ. The isolated blastocyst from which human ES cells are isolated may be produced by a number of methods well known to those skilled in the art, such as in vitro fertilization, intracytoplasmic sperm injection, and ooplasm transfer. In certain embodiments, the isolated human ES cells are grown on embryonic fibroblast cells including, but not limited to, mouse embryonic fibroblasts, human embryonic fibroblasts or fibroblast-like cells derived from adult human tissues. In other embodiments, the human ES cells are grown under feeder-free conditions.

A population of human ES cells derived from blastocysts, as described in the preferred embodiments, express specific markers of ES cells, including but not limited to, Oct-4, Nanog, Rex1, Sox-2, FGF4, Utf1, Thy1, Cripto1, ABCG2, Dppa5, hTERT, Connexin-43, Connexin-45. Human ES cells do not express markers characteristic of differentiated cells, such as Keratin 5, Keratin 15, Keratin 18, Sox-1, NFH (ectoderm); brachyury, Msx1, MyoD, HAND1, cardiac actin (mesoderm); GATA4, AFP, HNF-4a, HNF-30, albumin, and PDX 1 (endoderm). The human ES cells also express cell surface markers such as stage specific embryonic antigen 3 (SSEA-3), SSEA-4, tumor-recognition antigen 1-60 (TRA-1-60), TRA-1-81, Oct-4, E-cadherin, Connexin-43, and alkaline phosphatase. Expression levels may be detected by immunocytochemistry. The extensive molecular characterization of the human ES cell lines of the present disclosure may provide invaluable insight into early embryonic development.

In certain embodiments of the present disclosure, isolated human ES cells are cultured in a nutrient medium, preferably which comprises growth factors, and maintained by manual passaging. As used herein the term "growth factor" refers to proteins that bind to cell surface receptors with the primary result of activating cellular proliferation and differentiation through the activation of signaling pathways. The majority of growth factors/supplements are quite versatile and capable of stimulating cellular division in numerous different cell types, while the specificity of some growth factors is restricted to certain cell types. Growth factors may be used that are specific to pluripotent ES cells and their induction to differentiate into various lineages such as neurons, hepatocytes, cardiomyocytes, beta-islets, chondrocytes, osteoblast, myocytes, and the like. An example of ES cell media contains 80% DMEM/F-12, 15% ES-tested FBS, 5% Serum replacement, 1% nonessential amino acid solution, 1 mM glutamine (GIBCO), 0.1% beta mercaptoethanol, 4 ng/ml human bFGF and 10 ng/ml human Leukemia inhibitory factor (LIF). The method of manually passaging the cells is advantageous over the commonly used method of passaging by enzymatic treatment, because it helps to maintain the genetic stability of the cell line. Maintenance of the normal karyotype of a cell line is important for its use in therapeutic purposes.

Preferable, ES cells of the present disclosure exhibit high levels of telomerase activity as assessed by a non-radioactive PCR-based Syber-Green detection method. This is indicative of the high self-renewal capacity of the cells of the present disclosure for at least about 40 passages in culture, more preferably at least about 60 passages, and most preferable at least about 100 passages in culture. The human ES cells also preferably possess normal euploid karyotypes and show no gross alteration in chromosomes even after one year in culture.

The present disclosure further describes the unique characteristics of the human ES cells as evidenced by HLA and STR typing. HLA typing analyses play a pivotal role in stem cell-based transplantation therapies. The exploitation of tandemly repeated elements in the genome by STR genotyping has also become important in several fields including: genetic mapping, linkage analysis, and human identity testing. The presently disclosed human ES cell lines possess unique HLA and STR types, which will provide better matching during transplantation for the Indian population.

The human ES cells of the present disclosure are pluripotent in nature, and have the ability to differentiate into representatives of all three germ layers in vitro and in vivo. When injected into SCID mice, human ES cells differentiate into cells derived from all three embryonic germ layers including, but not limited to, (1) bone, cartilage, smooth muscle, striated muscle, hematopoietic cells (mesoderm), (2) liver, primitive gut and respiratory epithelium (endoderm), and (3) neurons, glial cells, hair follicles, and tooth buds (ectoderm). This characteristic may be confirmed by examination of the histological sections of the tumor formed in mice at the site of injection of human ES cells described herein.

The derived human ES cells are also capable of forming embryoid bodies (EBs) in suspension culture. As used herein, the term "embryoid bodies" refers to an aggregation of differentiated or undifferentiated pluripotent ES cells surrounded by a primitive endoderm generated in suspension culture. Embryoid bodies contain cells of all three lineages including ectoderm, mesoderm and endoderm. In mature human embryoid bodies, it is possible to discern cells bearing markers of various cell types, such as neuronal cells, haematopoietic cells, liver cells, cardiac muscle cells and pancreatic islet cells. The embryoid bodies and their detailed characterization may provide valuable insight into the determination of the fate of ES cells. Further, the differentiation of ES cells into desired phenotypes through employment of suitable growth factors and their supplements may be investigated.

In one method of generating EBs, suspension aggregates are allowed to differentiate for 10-14 days in ES medium without LIF. The EBs generated may express a set of lineage specific markers such as Keratin 5, Keratin 15, Keratin 18, Sox-1, NFH (ectoderm), Brachyury, Msx1, MyoD, HAND1, cardiac actin (mesoderm), GATA4, AFP, HNF-4alpha, HNF-30, albumin and PDX1 (endoderm). The unambiguous expression of a set of differentiated markers clearly demonstrates the differentiation potential of the human ES cell line, for example, wherein at least 80% of the differentiated cells may be neurons, 30-50% may be cardiomyocytes, 80-90% may be hepatocytes, and 40-60% may be pancreatic cells, depending on the culture conditions.

In certain embodiments, the human ES cells described herein may be used to screen compounds, for example, small molecules and drugs, for their effect on the cell population. The compounds can also be screened for cell toxicity or modulation of expression. In other embodiments, the human ES cells disclosed herein may be used to study the cellular and molecular biology of development, functional genomics, as well as the generation of differentiated cells for use in therapeutic or prophylactic transplantation, treatment, drug screening, or in vitro drug discovery. For example, the human ES cells can be used for genomic analysis, to produce mRNA, cDNA, or genomic libraries, to produce specific polyclonal or monoclonal antibodies, including, but not limited to, humanized monoclonal antibodies (WO 01/51616, specifically incorporated herein by reference), or to screen for the effects of different test compounds or biologically active molecules on human ES cells, as well as cells or tissues derived therefrom, such as pharmaceutical compounds in drug research. The test compounds or biologically active molecules screened may be derived, for example, from plants, plant-based extracts, or synthetic sources. Human ES cells can also be used to screen for factors (such as small molecule drugs, peptides, polynucleotides, and the like) or conditions (such as cell culture conditions or manipulations) that affect the characteristics of human ES cells in culture, and the differentiation of human ES cells into various specific cell and tissue types.

Recently, the use of stem cells in toxicology research has been reported (Davila et al., (2004) Toxicol. Sci. 79(2):214-23). The overwhelming benefit of stem cells, when applied to toxicology, evolves from their unique properties compared to primary human cells (i.e., unlimited proliferation ability, plasticity to generate other cell types, and a more readily available source of human cells). While in vitro differentiation of mouse ES cells to hepatocytes has been reported (Hamazaki et al., (2001) FEBS Lett. 18; 497(1):15-9), the utility of these differentiated hepatocytes as an in vitro screening model for potential drug candidates has not been extensively studied. Based on experiments with mouse ES cells, hepatocytes generated from mouse or human ES cells may prove to be a suitable alternative to conventional in vitro toxicity models for drug metabolism and toxicity studies.

The present disclosure describes the use of ES cell-derived hepatocytes to study xenobiotic-induced hepatotoxicity by measurement of the release of enzymes including, but not limited to, serum glutamate pyruvate amino-transferase (SGPT), serum glutamate oxalo-acetate aminotransferase (SGOT), alkaline phosphatase (ALP), and lactate dehydrogenase (LDH). Although the application is not limited to using ES cell-derived hepatocytes for studying toxicity, this cell type is particularly well-suited for toxicity testing because the characterization tests at the cellular, molecular, and functional level are well defined; high percentages of hepatocytes can be efficiently derived from ES cells; morphologically, hepatocytes are clearly distinguishable from other cell types, which reduces the confusion associated with a mixed population (see Kulkarni and Khanna, Functional hepatocyte-like cells derived from mouse embryonic stem cells: A novel in vitro hepatotoxicity model for drug screening, 2006, Toxicology In Vitro (in press), incorporated herein by reference). This concept may be employed as an alternative to conventional in vitro toxicity models for drug metabolism and toxicity studies, derived from hepatocytes the human ES-cells or other available human ES cell lines of the present disclosure.

Human ES cells share features with pluripotent human embryonal carcinoma (EC) cells. Putative human ES cells may therefore be characterized by morphology and by the expression of cell surface markers characteristic of human EC cells. Additionally, putative human ES cells may be characterized by developmental potential, karyotype and immortality. Examples of identifying characteristics of human ES cells are as follows.

a) Morphology: The colony morphology of human ES cells is similar to, but distinct from, mouse ES cells. Both mouse and human ES cells have the characteristic features of undifferentiated stem cells, with high nuclear/cytoplasmic ratios, prominent nucleoli, and compact colony formation. But colonies of human ES cells are flatter than mouse ES cell colonies, and individual ES cells can be easily distinguished.

b) Cell surface markers: A human ES cell line of the present disclosure is distinct from mouse ES cell lines based on the presence or absence of certain cell surface markers described below. The glycolipid cell surface markers SSEA 1 through 4 are differentially expressed by human versus mouse ES cells, and can be identified using antibodies for the antigens. The NTERA-2 CL.D1 cell line was chosen as a positive control in some of the experiments described herein because it has been extensively studied and reported in the literature, but other human EC cell lines may be used as well.

Mouse ES cells (ES J1) are used as a positive control for SSEA-1, and as a negative control for SSEA-3, SSEA-4, TRA-1-60, and TRA-1-81. Other routine negative controls include omission of the primary or secondary antibody and substitution of a primary antibody with unrelated specificity. Alkaline phosphatase may be detected following fixation of cells with 4% para-formaldehyde. The globo-series glycolipids SSEA-3 and SSEA-4 are consistently present on human EC cells. Differentiation of NTERA-2 CL.D1 cells in vitro results in the loss of SSEA-3, SSEA-4, TRA-1-60, and TRA-1-81 expression and the increased expression of the lacto-series glycolipid SSEA-1. This contrasts with undifferentiated mouse ES cells, which express SSEA-1, and neither SSEA-3 nor SSEA-4. Although the function of these antigens is unknown, their shared expression by Relicell™ hES1 cells and human EC cells suggests a close embryological similarity. Alkaline phosphatase will also be present on all human ES cells. A successful human ES cell culture of the present disclosure will correlate with these cell surface markers found in other established human ES cell lines.

c) Developmental potential by teratoma formation: Human ES cells of the present disclosure are pluripotent. When injected into SCID mice, a successful human ES cell line will differentiate into cells derived from all three embryonic germ layers including: bone, cartilage, smooth muscle, striated muscle, and hematopoietic cells (mesoderm); liver, primitive gut and respiratory epithelium (endoderm); and neurons, glial cells, hair follicles, and tooth buds (ectoderm).

d) Karyotype: Successful human ES cell lines have normal karyotypes. Both XX and XY cells lines can be derived. The normal karyotypes in human ES cell lines will be in contrast to the abnormal karyotype found in human EC cells, which are derived from spontaneously arising human germ cell tumors (teratocarcinomas). Although tumor-derived human EC cell lines have some properties in common with ES cell lines, all human EC cell lines derived to date are aneuploid. Thus, human ES cell lines and human EC cell lines can be distinguished by the normal karyotypes found in human ES cell lines and the abnormal karyotypes found in human EC lines. By "normal karyotype" it is meant that all chromosomes normally characteristic of the species are present and have not been noticeably altered. In addition, human ES cell line with a normal karyotype preferable maintain a karyotype which the chromosomes are euploid throughout prolonged culture. The normal karyotype of a human ES cell line suggest that this cell line will reflect normal differentiation.

e) Immortality: Immortal cells are capable of continuous indefinite replication in vitro. Continued proliferation for longer than one year of culture is sufficient evidence of immortality, as primary cell cultures without this property fail to continuously divide for this length of time. Preferably, human ES cells will continue to proliferate in vitro under appropriate culture conditions for longer than one year, and will maintain the developmental potential to contribute to all three embryonic germ layers. This developmental potential can be demonstrated by the injection of ES cells that have been cultured for a prolonged period (over a year) into SCID mice and then histologically examining the resulting tumors. Although karyotypic changes can occur randomly with prolonged culture, the majority of human ES cells should maintain a normal karyotype for longer than a year of continuous culture. This can be demonstrated by detection of the telomerase enzyme activity of the human ES cells at the later stages of propagation. High levels of telomerase activity are associated with cell proliferation during embryonic development and with cell transformation and cancers.

f) Culture conditions: Growth factor requirements to prevent differentiation are different for human ES cell lines of the present disclosure than for mouse ES cell lines. For mouse ES cells, the determination that LIF is able to support their self-renewal and proliferation as undifferentiated cells in the absence of feeders was a significant discovery. Unfortunately, LIF does not seem to have this ability with respect to human ES cell cultures (Jones, et al. (1998); Bongso et al., (2000) supra.

Alternatively, sources of human feeders including, but not limited to, human embryonic fibroblast, human foreskin, bone marrow mesenchymal cells, stromal cells of various adult origin, or any combinations thereof, may be used in the present disclosure as a substitute to mouse embryonic feeders (MEF) in order to grow human ES cells (with the objective of developing a xeno-free environment for human ES cell cultures). Nevertheless, the culture of human ES cells without feeders would be ideal. Not only would this eliminate a possible source of exogenous contamination with potential pathogens, it would also greatly simplify the logistics of ES cell culture, particularly on a larger scale. Conditioned medium from mouse embryo fibroblasts will support the proliferation of human ES cells cultured on the extracellular matrix preparation Matrigel (Invitrogen) in the absence of feeders (Carpenter et al., (2001) Nat. Biotechnol. 19(10):971-4). Although this provides some practical advantages, the active factor from the conditioned medium has not yet been identified, and this approach fails to eliminate the possibility of contamination from murine endogenous retroviruses.

g) Differentiation to extra-embryonic tissues: When grown on embryonic fibroblasts and allowed to grow for two weeks after achieving confluence (i.e., continuously covering the culture surface), human ES cells of the present disclosure spontaneously differentiate into neurons, cardiomyocytes, hepatocytes and pancreatic islet cells. The markers responsible for the aforesaid cell types can be detected by semiquantitative RT-PCR and immunocytochemistry using genes specific primers and antibodies to the respective gene of interest.

h) Differentiated stem cells in regenerative medicine: Human ES cells of the present disclosure may be induced to differentiate into particular phenotypes in vitro. Using such techniques may generate a pure population of a desired cell type, which can be injected into, for example, a damaged organ to repair injury. Such injury may be due to various diseases or conditions, such as, but not restricted to, neurodegenerative diseases, myocardial infarction, congestive heart failure, liver failure, and diabetes. Examples of neurodegenerative diseases, include but are not limited to stroke, spinal cord injury, Parkinson's disease, Alzheimer's disease, multiple sclerosis and the like. Therefore, differentiated human ES cells possess enormous potential in cell transplantation for cell replacement therapy or tissue regeneration. In addition, cell lines derived by the present disclosure can be used as a carrier vehicle for various therapeutically active molecules. For example, specific genes may be delivered to various sites of the human body, preferably in cells that are genetically manipulated and delivered to the target site for gene therapy.

i) Differentiated stem cells for drug screening and therapeutics: The present disclosure provides the possibility of using human ES cells and their unique capability to differentiate into the cells of all three lineages (ectoderm, mesoderm and endoderm) for pharmaceutical interventions and cell-based assays for drug discovery and in vitro toxicity testing. Another aspect of the present disclosure provides an opportunity to use these differentiated cells including, but not limited to, neuronal cells, cardiomyocytes, hepatocytes and beta-islets to screen various biological active molecules, for example, those derived from plant-based extracts and synthetic sources. The screening method can be used to develop novel drug molecules for various diseases such as, for example, Parkinson's diseases, Alzheimer's disease, Huntington disease, cardiac disorders, diabetes and hepatic diseases.

Along similar lines, mouse ES cell-derived hepatocytes were used to study xenobiotic-induced hepatotoxicity by measurement of the release of enzymes including, but not limited to, serum glutamate pyruvate amino-transferase (SGPT), serum glutamate oxalo-acetate aminotransferase (SGOT), alkaline phosphatase (ALP) and lactate dehydrogenase (LDH). Cells of the present disclosure can also be used to study drug-induced induction of cytochrome P450 isoforms including, but not limited to, CYP1A1, CYP2A6, CYP2B6, CYP2C9, CYP2E1, and CYP3A4, and to identify drug metabolite(s) using analytical techniques including, but not limited to, high performance liquid chromatography (HPLC), liquid chromatography-mass spectroscopy (LC-MS), and gas chromatography-mass spectroscopy (GC-MS).

The cells derived by the present disclosure can also be used for generation of both polyclonal and monoclonal antibodies for either research or therapeutic potential, preferably for generating humanized monoclonal antibodies for the treatment of various diseases.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the disclosed specific embodiments and still obtain a like or similar result without departing from the spirit and scope of the invention.

EXAMPLE 1

The present example discloses the preparation of blastocysts by in vitro fertilization.

1) Isolating Blastocysts

Blastocyst stage embryos (blastocysts) may be isolated from a variety of sources. These blastocysts may be isolated from recovered in vivo fertilized preimplantation embryos, or from in vitro fertilization (IVF) (for example, embryos fertilized by conventional insemination, intracytoplasmic sperm injection, or ooplasm transfer). Human blastocysts are obtained from couples or donors who voluntarily donate their surplus embryos. These embryos are used for research purposes after acquiring written and voluntary consent from these couples or donors. Alternatively, blastocysts may be derived by transfer of a somatic cell or cell nucleus into an enucleated oocyte of human or non-human origin, which is then stimulated to develop to the blastocyst stage. The blastocysts used may also have been cryopreserved, or result from embryos which were cryopreserved at an earlier stage and allowed to continue to develop into a blastocyst-stage embryo. Preferably, blastocysts of good morphological grade are used in the present disclosure, for example, blastocysts in which the ICM is well developed. The development of both the blastocyst and the inner cell mass will vary according to the species, and are well known to those of skill in the art. Embryos are cultured in medium conditions that maintain survival and enhance development into blastocyst stage embryos (Fong and Bongso, (1999), Hum. Reprod. 14(3): 774-81, incorporated herein by reference).

Institutional Ethics Committee approval was obtained before initiation of any studies disclosed herein using human blastocysts. Prior written consent was taken from individual donors for the donation of surplus embryos for this study after completion of infertility treatments. The protocol generally used to obtain viable embryos from infertility patients is described below:

2) In Vitro Fertilization

For IVF, a woman first must undergo pituitary suppression treatment down regulation with a GnRH agonist such as Leuprolein Acetate (Lupron). This treatment is followed by controlled ovarian hyperstimulation with injection of Gonadotrophin (hMG) for 7-12 days, during which growth of the follicles is monitored by ultrasonography and plasma estradiol levels. Ovulation is triggered by intramuscular injection of hCG 10,000 IU (Profasi) when at least one or more follicles are 18 mm in diameter.

3) Oocyte Retrieval and Recovery of Embryos

Figure 1:
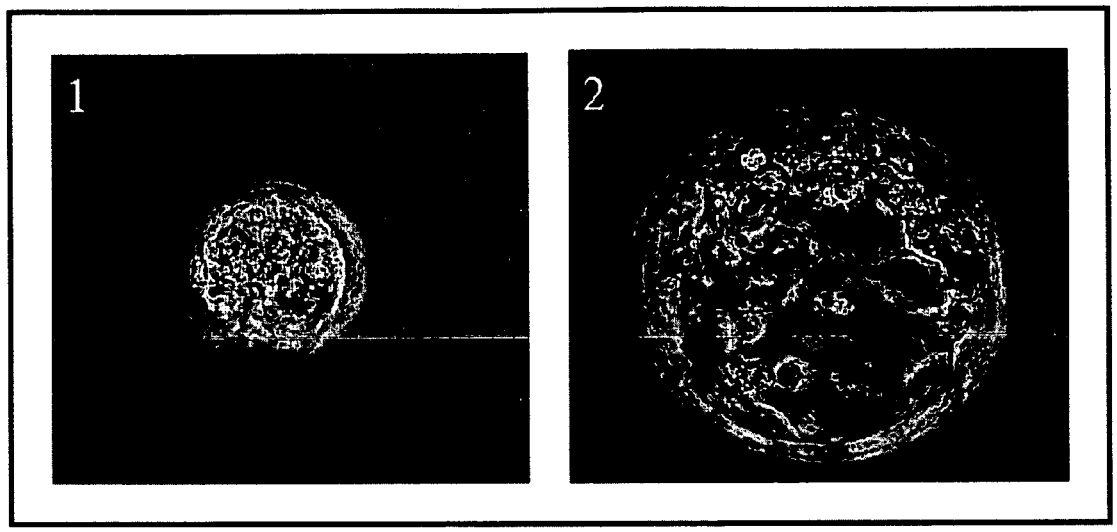
FIG. 1 shows photomicrographs of a human blastocyst at low (100×) and high (200×) magnification. This blastocyst was used to establish the Relicell™ hES1 cell line. Photograph 1.2 shows a day 6 blastocyst at high magnification with a clearly visible zona-pellucida, mono-layered trophectoderm and a poorly developed ICM. The grade of the embryo was Grade-C (See Gardner et al., (2000) Fertil. Sterility, 73:1155-58).

Oocyte retrieval is achieved by follicular aspiration at 34-36 hours under ultrasonography guidance. Fertilization is assessed by the presence of 2 pronuclei (2 PN) and the fertilized oocytes are transferred to embryo culture dish. Two fertilized oocytes (2 PN) per plate are transferred in 0.75-1 ml of cleavage medium (Quinn's cleavage Medium (Sage Biopharma Cat. # ART-1026)). These dishes are incubated in incubator in a 5% $CO_2$ environment at 37° C. until day 2. On day 2, the cleavage medium is changed. On day 3, blastocyst medium (QA Blastocytes Medium (Sage Biopharma Cat. # ART-1029)) replaces the cleavage medium and the embryos are cultured until day 5 to day 7, when expanded blastocysts are obtained. Medium is replaced every other day. After overnight culture, the embryos were monitored visually under a dissecting microscope. The integration was considered successful if the embryo developed into a morula or well-expanded blastocyst (FIGS. 1.1 and 1.2). Human ES cells as disclosed herein may be isolated from the morula stage to the blastocyst stage.

EXAMPLE 2

The present example discloses the derivation and storage of mouse embryonic fibroblast (feeder) cells.

1) Procurement of Pregnant Mice and Dissection

Mouse embryonic fibroblasts (MEFs) may be obtained from inbred C57 Black mice or other suitable strains. In an illustrative method, a mouse at 13.5 days of pregnancy/days post coitum (dpc) is sacrificed by cervical dislocation. The abdomen of the mouse is swabbed with 70% Isopropanol followed by a small incision. The viscera is exposed by pulling apart the abdominal skin in opposite directions. The uterus filled with embryos is seen in the posterior abdominal cavity. The uterus is dissected out with sterile forceps and scissors and placed into 50 ml screw capped conical centrifuge tube containing 20 ml of sterile Dulbecco's phosphate buffered saline, Ca- and Mg-free (GIBCO-BRL, Cat No. 14190-144). Uteri containing embryos are dissected out from all the pregnant animals sacrificed. The uteri are then washed 5-6 times in sterile Dulbecco's phosphate buffered saline, Ca- and Mg-free, inside a laminar flow hood. The embryos are harvested with the help of sterile, pointed forceps and scissors and then the placenta, membrane and soft tissues are removed.

Staging of Mice Embryos

Mouse embryos are staged under the dissecting microscope. Staging of the mouse embryos can be done according to a variety of criteria, the most general of which are described by Theiler in "The House Mouse: Atlas for Mouse Development" (1989) (incorporated herein by reference). Theiler's criteria are too broad to distinguish many important phases of early development and must therefore be supplemented by others, for example, cell number, somite number, or those characteristics used by Downs and Davis (1993), Dev. 118 (4):1255-66, incorporated herein by reference. Embryos of the same gestational age may differ in their stage of development. The stages recognized by Downs and Davis is applicable to F1 hybrids of C57 Black X CBA mice, inbred C57 black mice, and other closely related strains. The most acceptable stages for obtaining feeders for the purpose of growing human ES cells is Theiler stage 21 and 22. Theiler stage 21 is 13 dpc, with a range of 12.5-14 dpc, and the 52-55 somite stage. This stage is identified by an anterior, indented footplate, identifiable elbow and wrist, five rows of whiskers and a clearly apparent umbilical hernia. Additionally, hair follicles are absent and fingers are distally separate. Theiler stage 22 is recognized as 14 dpc, with a range of 13.5 to 15 dpc, and the 56-60 somite stage. The distinguishing features of this stage are distally separated fingers, an indentation between digits of the posterior foot-plate, and the presence of long bones of limbs and hair follicles in the pectoral, pelvic and trunk regions. Other features include the absence of open eyelids and hair follicles present in the cephalic regions.

3) Processing of Mice Embryos

The embryos were further processed by first discarding the head followed by all visceral organs under the dissecting microscope with the help of sterile pointed forceps. The carcass was then transferred into the lid of a 96 mm sterile petridish and minced properly with the help of sterile curved scissors. The minced mass is then transferred into a 50 ml conical centrifuge tube containing approximately 15-20 ml of 0.25% Trypsin-EDTA (GIBCO-BRL, Catalog No. 25200-056), pre-warmed at 37° C. The minced mass was then triturated 3-4 times in the Trypsin-EDTA solution with the help of a 10 ml pipette and passed 2-3 times though a 20 ml syringe fitted to a 18 gauge needle. The cell suspension was then incubated for 10-15 minutes at 37° C. The cell suspension was once again triturated through a 10 ml pipette. The trypsin in the cell suspension was inactivated by adding 20 ml of complete media (90% Dulbecco's modified Eagle's medium-High Glucose, 10% Fetal bovine serum, 1 mM L-Glutamine, 1% Non-Essential amino acids and 0.1 mM β-Mercaptoethanol) and the cell suspension was finally plated in tissue-culture flask. Thereafter, the cells were grown until confluency, with media change every alternate day with periodic monitoring.

4) Freezing of Mouse Embryonic Fibroblasts

Freezing of the cells was done at confluency in freezing media comprised of 60% Fetal bovine serum, 20% DMSO and 20% complete media. For freezing, the cells were resuspended in complete media and then mixed with freezing media in the ratio 1:1. This freezing suspension was then dispensed as 1 ml into cryovials such that 1 ml contains 5 million cells. These vials were then stored in liquid nitrogen for long-/term use.

5) Qualification of MEFs

Figure 2:
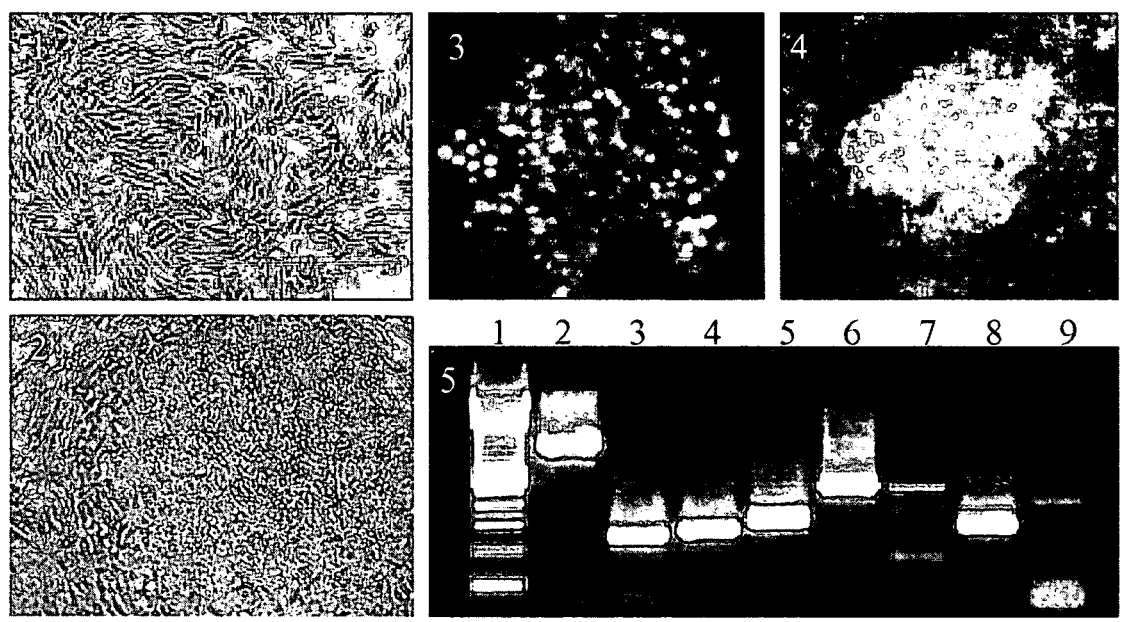
FIG. 2 shows photographs of mouse embryonic fibroblast (MEF) cells used for the culture and propagation of the Relicell™ hES1 cell line. Photograph 2.1 shows MEF cells at 80-90% confluency, 48-hours post plating; Photograph 2.2 shows an HESC colony on MEF for morphological analysis, and demonstrates healthy growth of the HESC colony grown; Photographs 2.3 and 2.4 show positive immunostaining of hESC on MEF with Oct-3/4 and SSEA-4 antibodies, respectively; Photograph 2.5 demonstrates the expression by RT-PCR of the following ES-cell markers in the HESC grown on MEF cells: GAPDH, Oct-4, Nanog, Rex1, TDGF1, Sox-2, Thy1, and FGF4 genes.

Every batch of feeders are qualified by examining human ES cells that have been grown on the MEF for 5 passages. The process of qualification involves assessment of critical parameters like morphological analysis of the human ES cell colonies (FIGS. 2.1 and 2.2), expression of ES cell markers by immunochemistry (FIGS. 2.3 and 2.4), RT-PCR (FIG. 2.5) and sterility check by endotoxin and mycoplasma testing. Only qualified feeders were used for isolating, passaging, and maintaining the Relicell™ hES1 cell line.

EXAMPLE 3

The present example describes the derivation and maintenance of human ES cells.

1) Inactivation and Plating of Mouse Embryonic Fibroblast (Feeder) Cells

The feeder cells stored in liquid nitrogen were thawed and cultured as needed. The vials were thawed by placing the frozen vials in a 37° C. water bath until the contents were semi-thawed. The contents were then collected in a tube and mixed with warm media to dilute the cryoprotectant. The cells were pelleted, resuspended, and plated in fresh MEF media (90% Dulbecco's modified Eagle's medium-High Glucose (GIBCO), 10% Fetal bovine serum (Hyclone), 1 mM L-Glutamine (GIBCO), 1% Non-Essential amino acids (GIBCO) and 0.1 mM β-Mercaptoethanol (Sigma)) in tissue culture flasks. Once the cells reached confluence, they were ready for inactivation. The cells were inactivated by Mitomycin C treatment or by gamma irradiation. Here, the cells were inactivated by Mitomycin C treatment for two and half hours. 10 ng/ml of Mitomycin C was used for inactivation at 37° C. and 5% $CO_2$. The cells were then washed several times for complete removal of Mitomycin C and then trypsinised using enzymes like trypsin-EDTA. These cells were then counted and plated onto 0.2% gelatinized plates at a concentration of $6.25 \times 10^4$ cells/cm$^2$. The cells were plated and incubated at 37° C. and 5% $CO_2$. These plates were then used for plating of isolated human ES cells.

2) ICM Isolation

Figure 3:
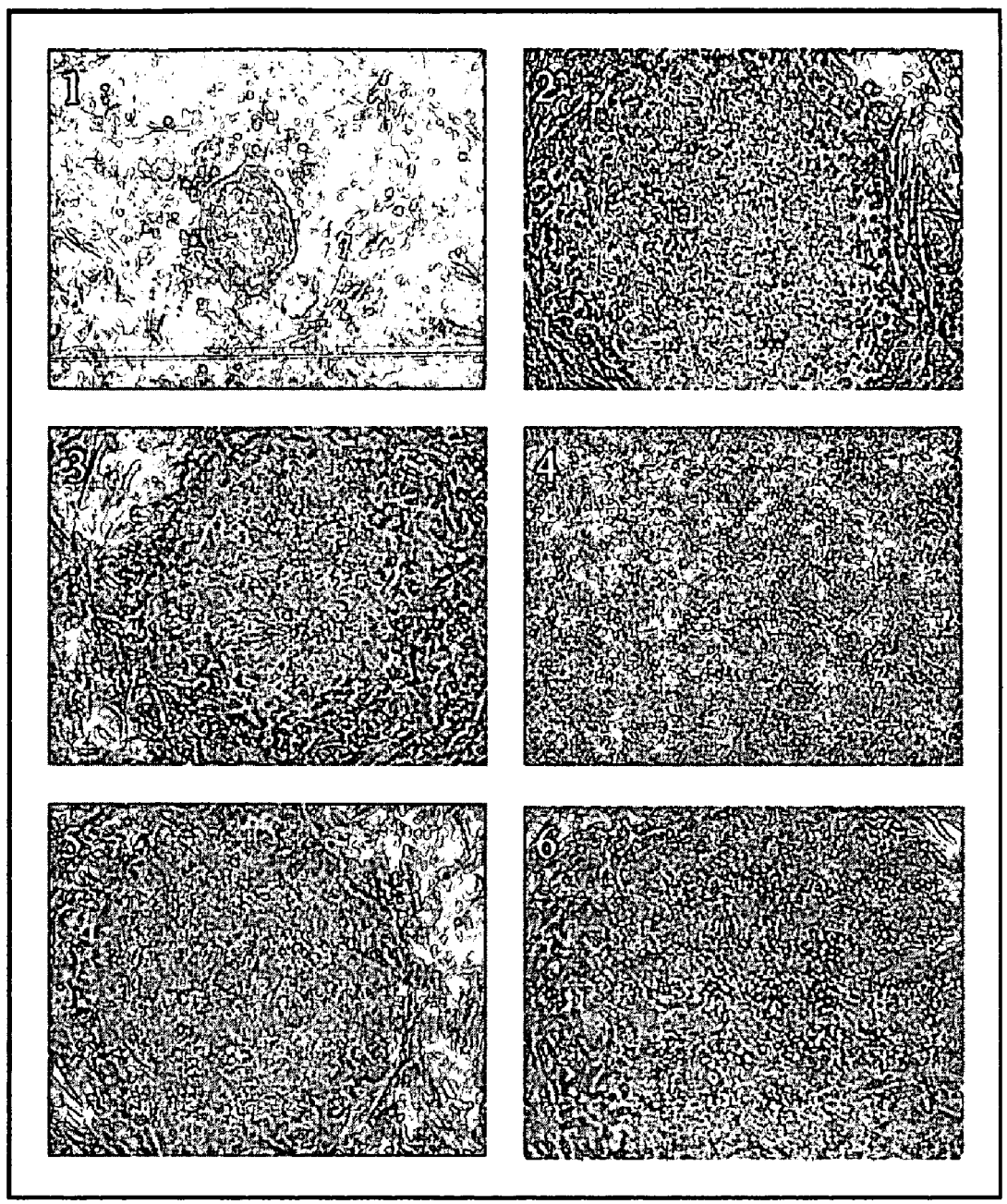
FIG. 3 shows a set of phase-contrast photomicrographs demonstrating the morphology of Relicell™ hES1 cells at progressive days of plating upon MEF layers in a media containing human LIF (10 ng/ml). The ICM attached after day 1 of plating and gradually expanded on the MEF cells after up to 12 days. At day 12, a human ES cell colony is isolated and passaged to propagate the cell line. Panel 1: day 1 of plating; Panel 2: day 4 of plating; Panel 3: day 5 of plating; Panel 4: day 6 of plating; Panel 5: day 8 of plating; and Panel 6: day 12 of plating.

To isolate ICM without risking cell loss, the whole embryo culture method was employed on day 6 of the embryo culture (FIGS. 1 and 3). The zona-pellucida was digested by 0.5% pronase for about 2 minutes. The ICM was then plated on mitotically-inactivated MEF cells. The human ES cell culture medium used in this technique consists of 80% DMEM/F-12 (GIBCO, with glucose 4500 mg/L), 15% ES tested FBS (Hyclone, USA), 5% Serum replacement (GIBCO, #10828-028), 1% nonessential amino acid solution (GIBCO), 1 mM glutamine (GIBCO), 0.1% beta mercaptoethanol (Sigma), 4 ng/ml human bFGF (R & D systems) and 10 ng/ml human Leukemia inhibitory factor (Sigma). After 7 days, the ICM clump was separated from other cells by mechanical dissociation with a micropipette. The ICM clump was then replated on a fresh feeder cell layer and fresh medium was added.

3) Culturing and Manual Passaging of human ES Cells

Figure 4:
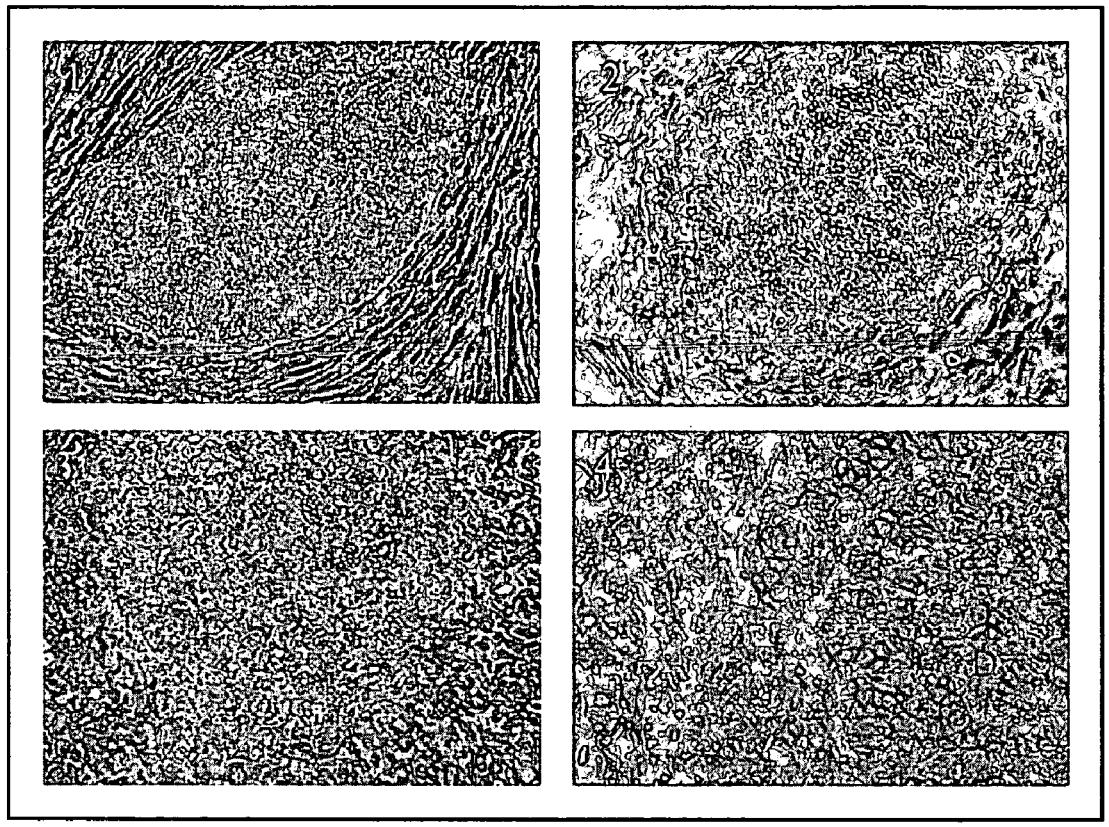
FIG. 4 is a set of phase-contrast photomicrographs demonstrating the morphology of undifferentiated HESC colonies at different passages starting from passage 10 up to passage 30. Photograph 3.1 shows a compact hESC colony at passage 10 on healthy looking MEF cells, which not only provide nutrition to the ES cells but also facilitate their maintenance in an undifferentiated state. Photograph 3.2 shows an hESC colony at passage 15. Photograph 3.3 shows the hESC at passage 20. Photograph 3.4, taken at a higher magnification (200×), demonstrates at passage 30 the distinct cell borders, high nucleus to cytoplasm ratio, and prominent nucleoli of undifferentiated hESC. The hESC were maintained in a medium comprising DMEM-F12 supplemented with 10% FBS and human LIF (10 ng/ml).

Subsequent passaging of the undifferentiated colonies was done by cutting the colonies systematically in clumps of about 100 cells using the sharp edge of a glass-pulled micropipette (FIG. 4). Selection was done to remove any unwanted differentiated areas of the colony. As soon as the clumps detached they were picked up by the same micropipette (with a bore size slightly bigger than the size of the clump) attached with a mouth aspiration set and transferred to a fresh fibroblast feeder layer. The culture system was maintained at a constant temperature of 37° C. by placing it in a 5% $CO_2$ incubator. The cell line Relicell™ hES1 has been grown for 40 passages in vitro and the cell line still consist primarily of cells with the morphology of human ES cells.

4) Cryopreservation of Human ES Cells

Three-day-old "good" undifferentiated human ES colonies were used for freezing. ES colonies along with the feeder layer were cut into small pieces using a cell scrapper. Then, the cells were collected in a sterile 15 ml centrifuge tube (Nunc) and spun at 200 G for 3 minutes. The supernatant was aspirated out. The volume of the cell pellet was measured and resuspended in ES media to bring the volume up to 0.5 ml. Next, an equal volume of freezing medium, which included 60% ES tested FBS (Hyclone, USA), 20% ES medium, and 20% DMSO HYBRIMAX (Sigma), was gently added to the human ES cell suspension with occasional swirling. Clumps of ES cells were transferred into a 1.2 ml cryo-vial (Nalge-Nunc, USA) containing freezing medium. The vials were slowly cooled (~1° c./min) in a freezing container (Sigma) to −80° C. and stored in liquid nitrogen the next day. On revival, post-thaw survivability of the frozen human ES cells was found to be about 50% or more.

EXAMPLE 4

The present example characterizes the isolated human ES cells.

1) Generation of Embryoid Bodies

To generate EBs, the human ES cell colonies need to be either cut into small pieces manually or dissociated into small pieces by enzymatic treatment with collagenase or trypsin EDTA. Here, the human ES cell colonies were cut manually into small pieces for embryoid body formation. The small pieces were then transferred in EB medium (80% DMEM/F-12 (Gibco, with glucose 4500 mg/L), 15% ES tested FBS (Hyclone, USA), 5% Serum replacement (Gibco, #10828-028), 1% nonessential amino acid solution (Gibco), 1 mM glutamine (Gibco), and 0.1% beta mercaptoethanol (Sigma)) to bacteriological plates for aggregation. The cell aggregates were allowed to grow in this medium for 10-14 days with media change every 3 days. The EBs generated by this method were characterized using cellular and molecular markers at different days in suspension cultures, for example, 0 day, 6 days, 10 days, and 14 days (FIGS. 9.1 to 9.4) to evaluate the in vitro differentiation potential of the human ES cell line.

2) Immunocytochemistry

Figure 5:
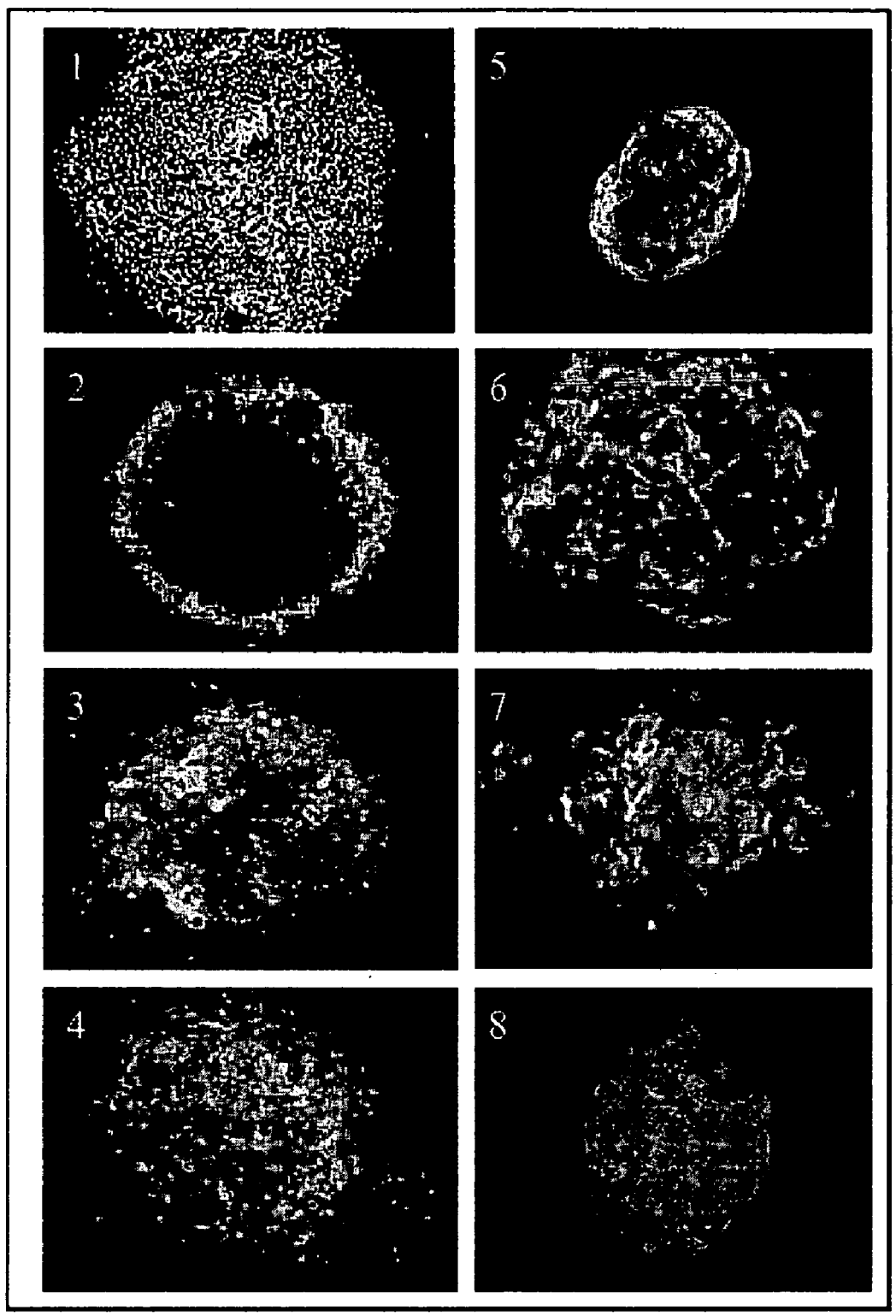
FIG. 5 is a set of eight photomicrographs showing phenotypic expression of different ES cell markers detected by immunocytochemistry for cells grown on MEF cells. Photograph 5.1 shows Oct-3/4 (+) hESC; Photograph 5.2 shows SSEA-3 (+) hESC; Photograph 5.3 shows SSEA-4 (+) hESC; Photograph 5.4 shows Tra-1-60 (+) HESC; Photograph 5.5 shows Tra-1-81 (+) hESC; Photograph 5.6 shows Connexin-43 (+) HESC; Photograph 5.7 shows E-cadherin (+) hESC; and Photograph 5.8 shows Alkaline phosphatase (+) immunostaining of hESC fixed in 4% paraformaldehyde. All of the markers analyzed are carbohydrate-rich cell-surface antigens except Oct-3/4, which is a POU5F1 promoter-encoded transcription factor, and Connexin-43, which is a gap junction molecule. The immunofluorescence analysis was carried out at every $5^{th}$ passage during the propagation of Relicell™ hES 1, and all antibodies used were FITC-labeled.

The cells grown in 2-well chamber slides (Becton Dickinson, USA) were fixed in freshly prepared 4% paraformaldehyde and permeabilized with 0.2% Triton X-100 in PBS. The non-specific binding sites were blocked with 1% bovine serum albumin in PBS. The cells were then incubated overnight at 4° C. with a primary antibody. Using this method, a panel of undifferentiated stem cell markers such as Oct-3/4, SSEA-3, SSEA-4, TRA-1-60, TRA-1-81, alkaline phosphatase, Connexin 43, E-cadherin were analyzed (FIGS. 5.1 to 5.8) as well as a group of differentiated markers such as nestin (Ectoderm), smooth muscle actin, brachyury (Mesoderm), AFP, and GATA4 (Endoderm) (FIGS. 10.1 to 10.5). Table 1 sets forth the relevant details of the antibodies used. Cells were then washed and incubated with the appropriate FITC-labeled secondary antibody at room temperature for 1 hour in the dark. Next, cells were counterstained with DAPI (1 ug/ml; Sigma). After mounting, the cells were observed under a fluorescence microscope (Nikon Eclipse E600) to evaluate immunopositive areas. The human ES cells expressed SSEA-3, SSEA-4, TRA-1-60, TRA-1-81, and Oct-4, which is typical of human ES cells, as well as E-cadherin and Connexin-43 (FIG. 5). The human ES cells also exhibited alkaline phosphatase activity as evidenced by fluorescence microscopy (FIG. 5.8). Further, the 14 day EBs stained positively for differentiation markers such as nestin (ectoderm), smooth muscle actin, brachyury (mesoderm), and GATA4 and AFP (endoderm) (FIG. 10).

TABLE 1

Details of antibodies used

| Name of the antibody | Manufacturer | Dilution used |
|---|---|---|
| Oct-3/4 | Santacruz, USA | 1:100 |
| SSEA-1 | ES cell characterization kit (Chemicon; Cat # SCR001) | 1:40 |
| SSEA-3 | | |
| SSEA-4 | | |
| TRA-1-60 | | |
| TRA-1-81 | | |
| Alkaline phosphatase | | |
| E-cadherin | Santacruz, USA | 1:200 |
| Connexin 43 | Santacruz, USA | 1:200 |
| Nestin | Chemicon, USA | 1:200 |
| Smooth muscle actin | Santacruz, USA | 1:100 |
| GATA4 | Santacruz, USA | 1:100 |

3) Gene Expression Analysis by RT-PCR

Figure 6:
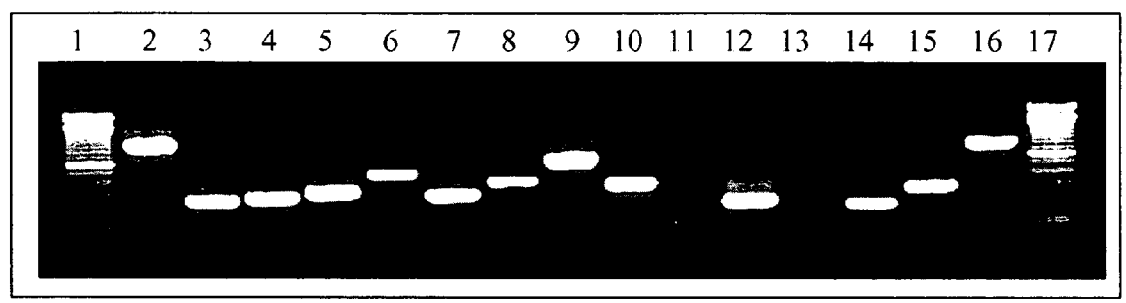
FIG. 6 is a photograph illustrating gene expression profiling of undifferentiated genes in the Relicell™ hES 1 cell line at passage 22, thereby establishing the pluripotency of the cell line in long-term culture. The RT-PCR analysis was carried out at every $5^{th}$ passage during the propagation of the Relicell™ hES 1 cell line. The markers include from left to right: Lane 1: 100 bp marker; Lane 2: GAPDH (892 bp); Lane 3: Oct-4 (247 bp); Lane 4: Nanog (262 bp); Lane 5: Rex1 (306 bp); Lane 6: Sox2 (448 bp); Lane 7: Thy1 (272 bp); Lane 8: FGF4 (374 bp); Lane 9: ABCG2 (684 bp); Lane 10: Dppa5 (353 bp); Lane 11: UTF1 (230 bp); Lane 12: Criptol (217 bp); Lane 13: FoxD3 (165 bp); Lane 14: hTERT (187 bp); Lane 15: Connexin-43 (295 bp); Lane 16: Connexin-45 (819 bp); and Lane 17: 100 bp marker. The enhanced expression of the hTERT gene is indicative of the high self-renewal capacity of the human ES cell line. GAPDH is used as a housekeeping gene control. Details of the primers used to amplify the undifferentiated genes are provided in Table 1.

Total RNA from the human ES cells disclosed herein was isolated by the TRIzol method (Invitrogen) according to the manufacturer's protocol. 1 μg of RNA treated with RNase-OUT ribonuclease inhibitor (Invitrogen) was used for cDNA synthesis. Reverse-transcription using Superscript reverse transcriptase-II (Invitrogen) and Oligo dT (Invitrogen) to prime the reaction also was carried out. PCR primers were selected to distinguish between cDNA and genomic DNA by using individual primers specific for different exons. 1 μl of cDNA was amplified by polymerase chain reaction (PCR) using Abgene 2×PCR master mix (Abgene, Surrey, UK) and appropriate primers. The expression of an array of markers was evaluated, including undifferentiated stem cell markers such as Oct-4, Nanog, Rex1, Sox-2, FGF4, Utf1, Thy1, Criptol, ABCG2, Dppa5, TERT, Connexin-43, and Connexin-45, and lineage specific markers such as Keratin 5, Keratin 15, Keratin 18, Sox-1, NFH (ectoderm), Brachyury, Msx1, MyoD, HAND1, cardiac actin (mesoderm), GATA4, AFP, HNF-4alpha, HNF-3beta, albumin, and PDX1 (endoderm). Table 2 sets forth the details of the primers. For all the genes, PCR was performed for 35 cycles, consisting of an initial denaturation at 94° C. for 1 minute followed by 35 cycles of 94° C. for 30 seconds, the annealing temperature of the respective gene primer for 45 seconds and 72° C. for 1 minute. The last cycle was followed by a final extension at 72° C. for 5 minutes. The human ES cells, at early as well as late passages, exhibited unambiguous expression of a set of genes associated with pluripotency, including Oct-4, Nanog, Rex-1, Sox-2, Criptol, FGF4, Thy1, Utf1, ABCG2, Dppa5, and hTERT, as well as gap junction proteins such as Connexin-43 and Connexin-45 (FIG. 6 and Table 3). HEF cells, which we used as a negative control, were devoid of the expression of any of these markers. Further, the expression profile of an exhaustive list of genes related to lineage specific differentiation was evaluated with 0-day, 6-day, 10-day, and 14-day-old EBs (FIG. 11 and Table 3). Consistent expression of early-stage ectodermal markers like Keratin 5, Keratin 15 and Keratin 18 from 6-days to 14-days of differentiation was observed in the EBs. Interesting, there was no expression of these markers on the O-day of differentiation, and the late-stage neuroectodermal markers Sox-1 and NFH were present only from 10-days to 14-days of differentiation (FIG. 11). Among the mesodermal lineage markers, Msx1, a pre-cardiac transcription factor, was expressed uniformly throughout the progressive days of differentiation. Other mesodermal markers, including brachyury, HAND1, MyoD and cardiac-actin, demonstrated weak or no expression in the human ES cells (FIG. 11). Similarly, early endodermal cell markers, including AFP, HNF-4α and HNF-3β, exhibited an expression on the 6th and 10th day of cell aggregate formation, while GATA4 levels demonstrated a transient increase from the 10-days up until the 14-days of suspension culture (FIG. 11). Very weak expressions were detected with the markers for mature hepatocytes, pancreatic islet cells, albumin and PDX1 respectively, thereby indicating the absence of mature endodermal derivatives (FIG. 11).

TABLE 2

Details of primers used

| Gene | Primer sequence | | Annealing temp (deg C.) | Expected Product size (bp) |
|---|---|---|---|---|
| *Housekeeping gene* | | | | |
| GAPDH | 5'-TGAAGGTCGGAGTCAACGGATTTGGT-3' | (SEQ ID NO:1) | 60 | 892 |
| | 5'-CATGTGGGCCATGAGGTCCACCAC-3' | (SEQ ID NO:2) | | |
| *Pluripotent stem cell markers* | | | | |
| Oct-4 | 5'-CGATGAAGCTGGAGAAGGAGAAGCTG-3' | (SEQ ID NO:3) | 58 | 247 |
| | 5'-CAAGGGCCGCAGCTTACACATGTTC-3' | (SEQ ID NO:4) | | |
| Nanog | 5'-CCTCCTCCATGGATCTGCTTATTCA-3' | (SEQ ID NO:5) | 52 | 262 |
| | 5'-CAGGTCTTCACCTGTTTGTAGCTGAG-3' | (SEQ ID NO:6) | | |
| Rex1 | 5'-GCGTACGCAAATTAAAGTCCAGA-3' | (SEQ ID NO:7) | 56 | 306 |
| | 5'-CAGCATCCTAAACAGCTCGCAGAAT-3' | (SEQ ID NO:8) | | |
| Sox2 | 5'-CCCCCGGCGGCAATAGCA-3' | (SEQ ID NO:9) | 55 | 448 |
| | 5'-TCGGCGCCGGGGAGATACAT-3' | (SEQ ID NO:10) | | |
| Thy1 | 5'-CATGAGAATACCAGCAGTTCACCCA-3' | (SEQ ID NO:11) | 55 | 272 |
| | 5'-CACTTGACCAGTTTGTCTCTGAGCA-3' | (SEQ ID NO:12) | | |
| FGF 4 | 5"-CTACAACGCCTACGAGTCCTACA-3' | (SEQ ID NO:13) | 53 | 370 |
| | 5'-GTTGCACCAGAAAAGTCAGAGTTG-3' | (SEQ ID NO:14) | | |
| ABCG2 | 5'-GTTTATCCGTGGTGTGTCTGG-3' | (SEQ ID NO:15) | 62 | 684 |
| | 5'-CTGAGCTATAGAGGCCTGGG-3' | (SEQ ID NO:16) | | |
| Dppa5 | 5'-ATGGGAACTCTCCCGGCACG-3' | (SEQ ID NO:17) | 62 | 353 |
| | 5'-TCACTTCATCCAAGGGCCTA-3' | (SEQ ID NO:18) | | |
| Utf1 | 5'-ACCAGCTGCTGACCTTGAAC-3' | (SEQ ID NO:19) | 60 | 230 |
| | 5'-TTGAACGTACCCAAGAACGA-3' | (SEQ ID NO:20) | | |
| Cripto1 | 5'-ACAGAACCTGCTGCCTGAAT-3' | (SEQ ID NO:21) | 62 | 217 |
| | 5'-ATCACAGCCGGGTAGAAATG-3' | (SEQ ID NO:22) | | |
| hTERT | 5'-AGCTATGCCCGGACCTCTAT-3' | (SEQ ID NO:23) | 60 | 165 |
| | 5'-GCCTGCAGCAGGAGGATCTT-3' | (SEQ ID NO:24) | | |
| *Gap Junction Proteins* | | | | |
| Connexin 43 | 5'-TACCATGCGACCAGTGGTGCGCT-3' | (SEQ ID NO:25) | 64 | 295 |
| | 5'-GAATTCTGGTTATCATCGGGGAA-3' | (SEQ ID NO:26) | | |
| Connexin 45 | 5'-CTATGCAATGCGCTGGAAACAACA-3' | (SEQ ID NO:27) | 64 | 819 |
| | 5'-CCCTGATTTGCTACTGGCAGT-3' | (SEQ ID NO:28) | | |
| *Ectodermal markers* | | | | |
| Keratin 8 | 5'-TGAGGTCAAGGCACAGTACG-3' | (SEQ ID NO:29) | 60 | 161 |
| | 5'-TGATGTTCCGGTTCATCTCA-3' | (SEQ ID NO:30) | | |
| Keratin 15 | 5'-CACAGTCTGCTGAGGTTGGA-3' | (SEQ ID NO:31) | 62 | 196 |
| | 5'-GAGCTGCTCCATCTGTAGGG-3' | (SEQ ID NO:32) | | |
| Keratin 18 | 5'-GGAGGTGGAAGCCGAAGTAT-3' | (SEQ ID NO:33) | 60 | 164 |
| | 5'-GAGAGGAGACCACCATCGCC-3' | (SEQ ID NO:34) | | |
| Sox-1 | 5'-TACAGCCCCATCTCCAACTC-3' | (SEQ ID NO:35) | 60 | 201 |
| | 5'-GCTCCGACTTCACCAGAGAG-3' | (SEQ ID NO:36) | | |
| NFH | 5'-TGAACACAGACGCTATGCGCTCAG-3' | (SEQ ID NO:37) | 58 | 400 |
| | 5'-CACCTTTATGTGAGTGGACACAGAG-3' | (SEQ ID NO:38) | | |

TABLE 2-continued

Details of primers used

| Gene | Primer sequence | | Annealing temp (deg C.) | Expected Product size (bp) |
|---|---|---|---|---|
| Mesodermal markers | | | | |
| Brachyury | 5'-TAAGGTGGATCTTCAGGTAGC-3'<br>5'-CATCTCATTGGTGAGCTCCCT-3' | (SEQ ID NO:39)<br>(SEQ ID NO:40) | 60 | 251 |
| MyoD | 5'-GTCGAGCCTAGACTGCCTGT-3'<br>5'-GGTATATCGGGTTGGGGTTC-3' | (SEQ ID NO:41)<br>(SEQ ID NO:42) | 60 | 217 |
| Msx1 | 5'-CCTTCCCTTTAACCCTCACAC-3'<br>5'-CCGATTTCTCTGCGCTTTTC-3' | (SEQ ID NO:43)<br>(SEQ ID NO:44) | 62 | 287 |
| HAND1 | 5'-GCCTAGCCACCACTGCGCTTTC-3'<br>5'-CGGCTCACTGGTTTAACTCC-3' | (SEQ ID NO:45)<br>(SEQ ID NO:46) | 62 | 389 |
| Cardiac-Actin | 5'-TCTATGAGGGCTACGCTTTG-3'<br>5'-CCTGACTGGAAGGTAGATGG-3' | (SEQ ID NO:47)<br>(SEQ ID NO:48) | 50 | 630 |
| Endodermal markers | | | | |
| AFP | 5'-AGAACCTGTCACAAGCTGTG-3'<br>5'-GACAGCAAGCTGAGGATGTC-3' | (SEQ ID NO:49)<br>(SEQ ID NO:50) | 62 | 577 |
| GATA4 | 5'-CTCCTTCAGGCAGTGAGAGC-3'<br>5'-GAGATGCAGTGTGCTCGTGC-3' | (SEQ ID NO:51)<br>(SEQ ID NO:52) | 52 | 680 |
| HNF-4alfa | 5'-TCTCATGTTGAAGCCACTGC-3'<br>5'-GGTTTGTTTCTCGGGTTGA-3' | (SEQ ID NO:53)<br>(SEQ ID NO:54) | 50 | 501 |
| HNF-3beta | 5'-GACAAGTGAGAGAGCAAGTG-3'<br>5'-ACAGTAGTGGAAACCGGAG-3' | (SEQ ID NO:55)<br>(SEQ ID NO:56) | 56 | 237 |
| Albumin | 5'-CCTTTGGCACAATGAAGTGGGTAACC-3'<br>5'-CAGCAGTCAGCCATTTCACCATAGG-3' | (SEQ ID NO:57)<br>(SEQ ID NO:58) | 58 | 450 |
| PDX1 | 5'-GTCCTGGAGGAGCCCAAC-3'<br>5'-GCAGTCCTGCTCAGGCTC-3' | (SEQ ID NO:59)<br>(SEQ ID NO:60) | 62 | 362 |

TABLE 3

Summary of gene expression analysis

| | | Observed expression | | |
|---|---|---|---|---|
| Serial Number | Name of the gene | Relicell™ hES1 | BG01 human ES cell line, as reported in (Brimble, et. al., 2004, supra) | HEF |
| Housekeeping gene | | | | |
| 1. | GAPDH | + | + | + |
| Pluripotent stem cell markers | | | | |
| 2. | Oct-3/4 | + | + | − |
| 3. | Nanog | + | + | − |
| 4. | Rex1 | + | + | − |
| 5. | TDGF1 | + | + | − |
| 6. | Thy1 | + | NR | + |
| 7. | Sox-2 | + | + | − |
| 8. | FGF4 | + | NR | − |
| 9. | Utf1 | + | + | − |
| 10. | ABCG2 | + | + | − |
| 11. | Dppa5 | + | + | + |
| 12. | Cripto | + | + | − |
| 13. | TERT | + | + | − |
| Gap junction proteins | | | | |
| 14. | Connexin 43 | + | + | − |
| 15. | Connexin 45 | + | + | − |
| Ectodermal markers in cell aggregates | | | | |
| 16. | Keratin 8 | + | + | − |
| 17. | Keratin 15 | + | + | − |
| 18. | Keratin 18 | + | + | − |
| 19. | NFH | + | + | − |
| 20. | Sox-1 | + | + | − |
| Mesodermal markers in cell aggregates | | | | |
| 21. | Brachyury | + | + | − |
| 22. | MyoD | + | + | − |
| 23. | Msx1 | + | + | + |
| 24. | HAND1 | + | + | − |
| 25. | C-actin | − | + | − |
| Endodermal markers in cell aggregates | | | | |
| 26. | GATA4 | + | + | − |
| 27. | AFP | + | + | − |
| 28. | HNF4a | − | NR | − |

TABLE 3-continued

Summary of gene expression analysis

| | | Observed expression | | |
|---|---|---|---|---|
| Serial Number | Name of the gene | Relicell ™ hES1 | BG01 human ES cell line, as reported in (Brimble, et. al., 2004, supra) | HEF |
| 29. | HNF3b | + | + | − |
| 30. | Albumin | − | NR | − |
| 31. | PDX1 | + | + | − |

4) HLA Typing

Since the spectrum of HLA antigens expressed on human ES cells is a clinically relevant characteristic, the HLA profile of the ReliCell™ hES1 cell line was generated. Briefly, HLA DNA typing was performed by utilizing an adopted hybridization of PCR-amplified DNA with sequence specific oligonucleotide probes (SSOP) as the primary technology for HLA typing (Tepnel Lifecodes Corporation, Wythenshawe, Manchester, UK). Assays were performed to analyze the HLA-A, HLA-B, HLA-C, HLA-DRB, and HLA-DQB loci.

TABLE 4

| | HLA-A | HLA-B | HLA-C | HLA-DRB1 | HLA-DQB1 |
|---|---|---|---|---|---|
| Relicell ® hES1 | A*01 | B*5601 | 01 | 01 | 05 |
| | A*02 | A*35 | 04 | 01 | 05 |

As shown in Table 4, the results document that the ReliCell™ HES1 cell line represents a range of HLA haplotypes with alleles HLA-A, HLA-B, HLA-C, HLA-DRB1, and HLA-DQB1.

5) STR Typing

DNA fingerprints of the ReliCell™ hES1 cell line were generated. Loci analyzed for STR analysis included D5S818, D13S317, D7S820, D16S539, vWA, TH01, Amelogenin, TP0X and CSF1P0 (multiplex-PCR-based PowerPlex 1.2 kit (Promega, Madison, Wis., USA)). The results are shown in Table 5. All of the loci included in this set are true tetranucleotide repeats. The amplicons were separated by electrophoresis and analyzed using Genotyper® 2.0 software from Applied Biosystems. From the study of these nine STR loci, it is clear that the cell line is derived from an embryo of Indian origin, which is different from the cell lines reported so far. These fingerprinting results also provide useful information of the cell lines after distribution of the cell line.

TABLE 5

| D5S818 | D13S317 | D7S820 | D16S539 | VWA | TH01 | TP0X | CSF1P0 | Amelogenin |
|---|---|---|---|---|---|---|---|---|
| 11, 12 | 10, 11 | 9, 12 | 11, 12 | 18 | 9 | 10, 11 | 10, 11 | X |

6) Karyotype

Karyotyping of the isolated human ES cells was performed using standard methods of colcemid arrest and G-banding technique. Briefly, human ES cells were cultured in a 60 mm culture dishes until 60% confluenct. The cells were incubated with ethidium bromide (12 ug/ml) for 40 minutes at 37° C., 5% $CO_2$, followed by colcemid (120 ng/mL) treatment for 40 minutes. Next, the cells were dissociated with pre-warmed 0.25% trypsin-EDTA. The cells were then collected by centrifugation, resuspended in hypotonic KCl solution (0.075 M) for 15 minutes, and fixed in Carnoy's fixative (glacial acetic acid:methanol; 3:1). Metaphase spreads were prepared on wet glass microscope slides, air dried, baked at 90° C. for an hour, and Giemsa staining was performed. Twenty metaphases were fully karyotyped using an Olympus BX40 microscope and images were captured using the Cytovision digital imaging system.

7) Telomerase Assay

Figure 8:
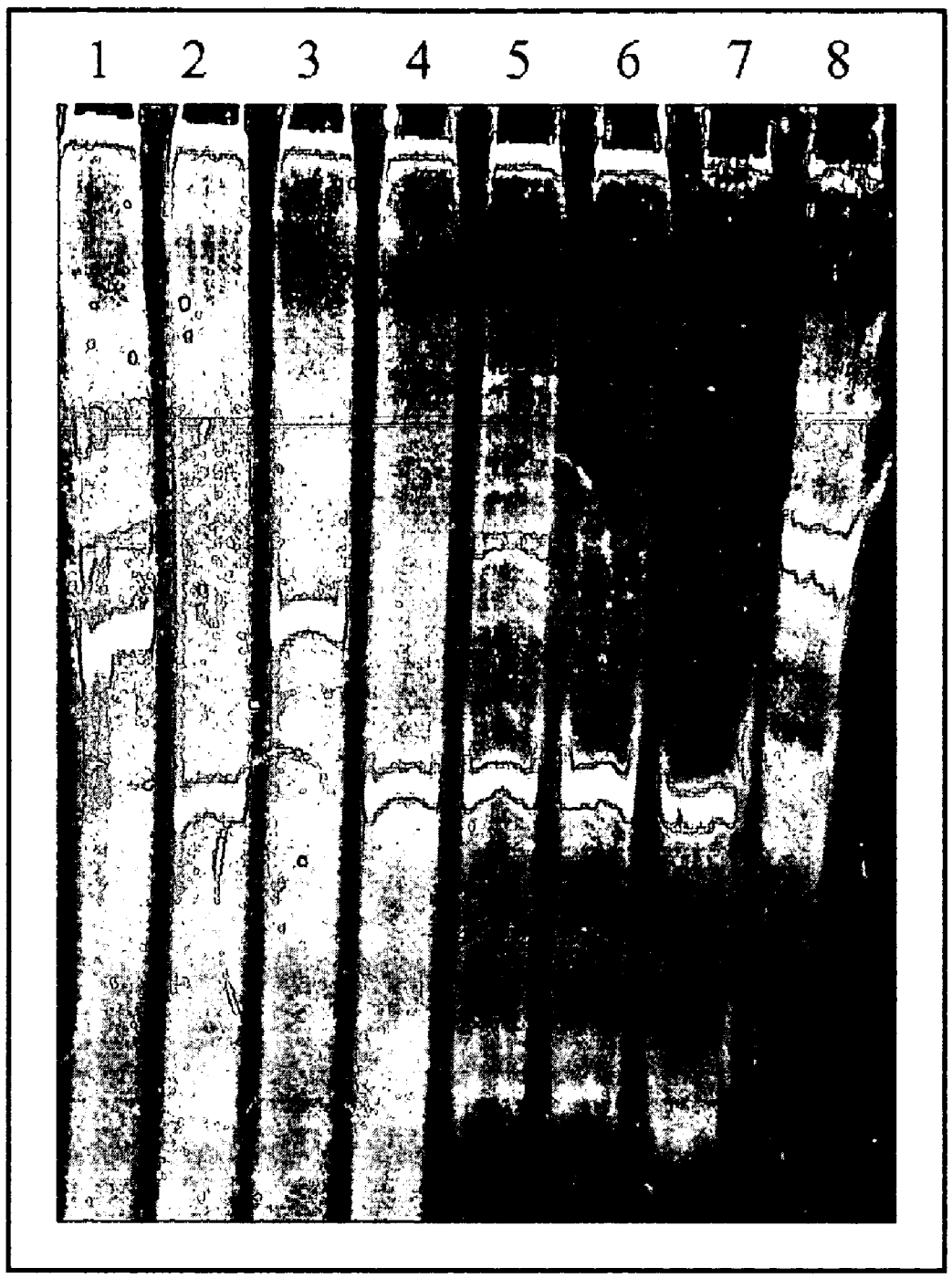
FIG. 8 is a picture of a 1.5% agarose gel showing substantial telomerase activity in the ReliCell™ hES1 cell line at passage 37 using PCR-based SYBER-Green staining. 6 μg of total protein were loaded for each assay. Lane 1: NTERA-2; Lane 2: NTERA-2 (Heat inactivated); Lane 3: MEF; Lane 4.

A telomerase assay was performed using non-radioisotopic gel-based standard TRAP (Telomerase Repeat Amplification) protocol (Zhang et al., (2000) Cell Res., 10(1):71-7 and Rubiano et al. (2003), Mem. Inst. Oswaldo Cruz., 98(5): 693-5) using a TRAPeze telomerase detection kit by Chemicon, USA (Catalog No. S7700). Approximately, 50-70 colonies of the human ES cells were pelleted and lysed using 200 µl of 1× CHAPS lysis buffer. The cell suspension in 1× CHAPS lysis buffer was incubated in ice for 30 minutes and then centrifuged for 20 minutes at 12,000 g at 4° C. The supernatant was quickly frozen and stored at −80° C. The total protein was estimated using a Bradford assay. The telomerase assay was performed using 1-6 µg of total extract. Heat inactivated samples served as negative controls for each assay. For telomerase PCR, the master mix was prepared by adding dNTP, TRAP Primer mix, TS primer and TAQ polymerase according to kit instructions. Next, the cell extract was added and the total reaction volume was maintained at 50 µl. A two-step PCR reaction was performed (94° C. for 30 seconds and 59° C. for 30 seconds) for 33 to 35 cycles. The PCR products were electrophoresed on a 12.5% non-denaturing polyacrylamide vertical gel at 400 volts until the xylenecyanol dye front reached two thirds of the entire run length. The gel was then stained with 1:5000 dilution of SYBR GREEN I dye (Molecular Probes, Catalog No. S-7567), visualized under a UV transilluminator, and photographed using a gel documentation system. The relative quantitation of the telomerase product generated (TPG) was done according to the method of Zhang et al. (2003)," Cell Research, 2000, 10(1):71-80. The TPB is explained by the formula: TPG={[(TP−B)/TI]/[(R8−B)/RI]}. Where, TP is telomerase product generated in test extract; B is telomerase product generated in Blank lysis buffer; R8 is telomerase product generated in Quantification standard, TSR8 control template; TI is Internal control of test extract; and R1 is Internal control of quantification standard, TSR8 control template. FIG. 8 shows high telomerase activity of ReliCell™ hES1 at passage 37, with NTERA-2 hEC cells as a positive control and MEF as the negative control.

8) Sterility and Pathogen Testing

Extensive bacterial and fungal tests were performed on the Relicell™ hES1 cell cultures. The cultures were routinely monitored and reported at 48 hour, 14 days and 21 days of incubation. Additionally, endotoxin and mycoplasma testing were performed using a Hoechst Assay for each culture. Finally, the cultures were screened for the presence of human pathogens including HIV-1, HIV-2, Human T-Cell Lymphotrophic Virus I/II, HSV1, HSV2, EBV, CMV, Hepatitis B Virus and Hepatitis C Virus.

9) Teratoma Formation

Figure 7:
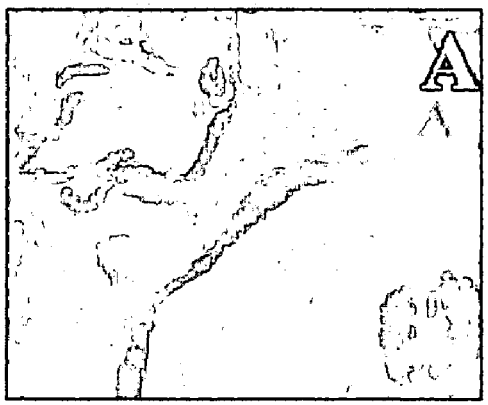
FIG. 7 shows an analysis of a teratoma formed after the injection of ReliCell™ hES1 cells into a SCID mouse. A pluripotent hESC line will differentiate into cells derived from all three embryonic germ layers when injected into SCID mice. Panel A: low power view of the teratoma; Panel B: demonstration of endoderm derivation (intestinal epithelium); Panels C and D: demonstration of ectoderm derivation (neural tissue); and Panels E and F: demonstration of mesoderm derivation (blood cells and bone, respectively).
Figure 7:
Figure 7:
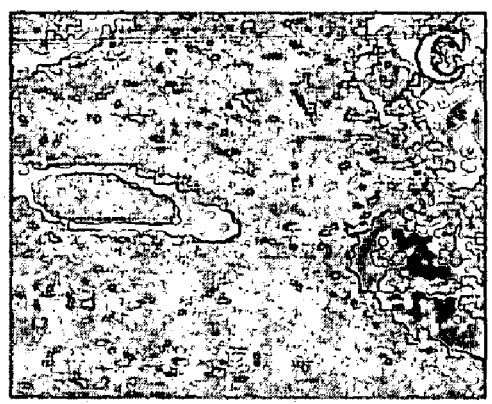
Figure 7:
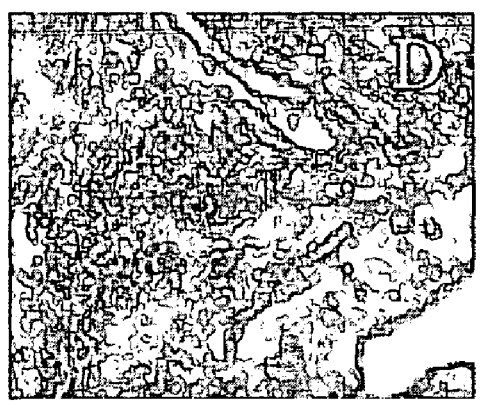
Figure 7:
Figure 7:
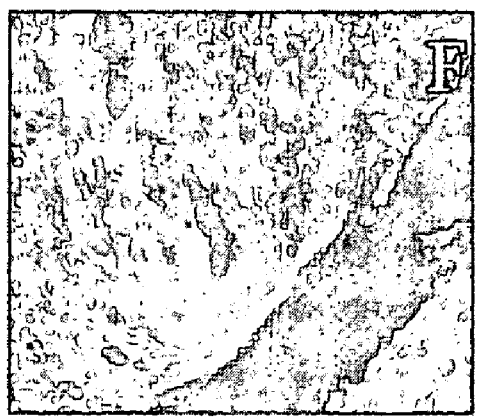

Adult nude mice were used for teratoma formation study. The undifferentiated human ES cell suspension (5-10 million cells per animal) was injected into an animal intramuscularly. After injection, the animal was kept in an individual filter top cage. These cages were housed in special animal isolators to prevent any possible infection. After 8-10 weeks, the animals were sacrificed with an overdose of Ketamine (100 mg/kg i.p.) and were transcardially perfused with heparin saline (0.1 heparin in 0.9% saline) followed by 4% paraformaldehyde prepared in phosphate buffered saline. The tumor was dissected out of the animal and fixed overnight in 4% paraformaldehyde along with 20% sucrose. The tumor was sectioned (20 um) using a cyro-microtome, and sections were collected on gelatin-coated slides. The tumor sections were stained with Hematoxylin/Eosin and observed under the microscope for cells belonging to the three germ layers, ectoderm, mesoderm, and endoderm. FIG. 7 shows the results of this experiment. All animal experiments were carried out following the guidelines of the Institutional animal ethics committee.

10) Establishment of In vitro Hepatotoxicity Model Using Differentiated Hepatocytes From Mouse ES Cells Mouse ES cells were differentiated into hepatocytes by the formation of EBs in a medium without LIF. After 4 days in suspension, 15-20 EBs were plated onto 35 mm culture dishes pre-coated with 1% matrigel (BD Biosciences, USA), and allowed to differentiate for 20-25 days. Concentration of growth factors, cytokines (e.g., bone morphogenetic proteins (BMP2 and BMP4), hepatocyte growth factor (HGF), acidic-fibroblast growth factor (aFGF), and basic-FGF (bFGF)) and corticosteroids (e.g., dexamethasone) were optimized for hepatic differentiation. The differentiated cells obtained were confirmed to be hepatocytes by checking the positive expression of hepatic markers by RT-PCR and immunocytochemistry. HepG2, a human hepatocarcinoma cell line, at a sub-confluent stage (generally 48-hours after plating) were used as a positive control to optimize the hepatotoxicity models based on differentiated ES cells. HepG2 cells were exposed to $CCl_4$ (Sigma) for a period of time (30, 90, 120, 150, 180 and 240 minutes) and in a dose-dependent manner (0.1%, 0.3%, 0.6% and 1.0%). Based on these observations, a 0.6% dose of $CCl_4$ and an exposure time of 180 min were selected for experiments with hepatocytes differentiated from mouse ES cells (day 20) (FIG. 13). $CCl_4$ was prepared in DPBS (Gibco-BRL, USA) containing 5% FBS. At the end of the incubation period, supernatant was collected and centrifuged at 1000 rpm for 2 minutes. This supernatant was used to determine SGOT, SGPT, LDH and ALP levels. The cells were dislodged using a cell scraper, and the cell suspension was collected in an eppendorf tube. This cell suspension was centrifuged at 2000 rpm for 4 min, and the cell pellet was dissolved in 200 µl of M-PER lysis buffer (Pierce, USA) for protein determination.

The cell supernatant was used for the determination of SGPT, SGOT, ALP, and LDH levels, per the manufacturer's protocol. For SGPT and SGOT, ERBA kits (manul.) were used, and for LDH and ALP, HUMAN kits were used. The samples were analyzed using a Konelab-20i autoanalyser (Thermo Clinical Lab Systems, Finland). The levels were expressed as units/Liter.

0.6% $CCl_4$ caused time-dependent increases in SGOT, SGPT, ALP and LDH levels, indicating increasing hepatocyte damage with time. Maximum release of these enzymes was seen at 180 minutes. Pretreatment (24 hr, 25 µM) with N-acetylcysteine effectively blocked the increase in the release of these enzymes. This indicates that pretreatment with N-acetylcysteine prevents the hepatocyte damage induced by $CCl_4$ (FIG. 13).

EXAMPLE 4

The present example demonstrates the in vitro differentiation potential of Relicell™ hES1.

To initiate differentiation, human ES cells were induced to undergo EB formation in suspension culture by mechanically desegregating the colonies into small to medium size pieces consisting of 100-150 cells on bacteriological dishes for 6-14 days without feeder layers in a basal medium without LIF. The age of the EBs for differentiation induction into different phenotypes belonging to separate germ layers was decided on the basis of the expression profile of the lineage specific markers in the EBs as evidenced by RT-PCR.

Neuroectodermal differentiation: To determine the potential of the human ES cell line to differentiate into neurons, a multi-step protocol was followed. Neural precursors were selected by incubating 6-day-old EBs in serum free ITSFn medium for 7-10 days. The cells were then expanded in N2 medium containing DMEM/F12 supplemented with bFGF (10 ng/ml) and EGF (10 ng/ml). The differentiation step involved the removal of bFGF, and culturing the cells in the presence of N2 medium supplemented with GDNF (5 ng/ml) for 2-3 weeks. Expression of MAP-2 (1:200, chemicon), a neuronal cell marker, was evaluated by immunoflourescence analysis to confirm neuronal differentiation. Other methods for differentiating human ES cells into cells of neuroectodermal are disclosed in U.S. Ser. Nos. 10/798,790 and 10/930, 675, each of which is incorporated herein by reference.

Mesodermal differentiation: After generation of EBs, 8-day-old EBs were seeded onto 35 mm tissue culture dishes (Nunc, Roskilde, Denmark) pre-coated with 0.1% gelatin (Sigma, USA) in 80% DMEM media supplemented with 15% FBS, 1% nonessential amino acid, 1 mM glutamine, 0.1% beta-mercaptoethanol and 12.5 ng/ml human basic fibroblast growth factor. Rhythmic beating of EBs appearing on the 17-18$^{th}$ day of differentiation culture, indicative of cardiac muscle differentiation, was carefully monitored by daily observation of cultures under a phase contrast microscope for more than 45 days. Intact contracting areas within the EBs were mechanically dissected using a sterile glass-pulled pipette under the stereomicroscope and plated onto gelatin-coated 2-well chambered glass slides (Nunc, Roskilde, Denmark) for further characterization.

Endodermal differentiation: To induce pancreatic differentiation, the classical protocol of Segev et al., (2004) Stem Cells 22(3):265-74, was followed. 10-day-old EBs were plated onto 35 mm plastic tissue culture plates (Nunc, Roskilde, Denmark) and grown in medium I containing DMEM F/12, insulin (10 ng/l), transferrin (6.7 ng/l), selenium (5.5 mg/l) and 1 mM L-glutamine (all from Gibco), with a supplement of 5 µg/ml of Fibronectin (Sigma). After one week, the cells were dissociated with 0.05% Trypsin-EDTA (Gibco-Invitrogen) and re-plated onto 35 mm plastic tissue culture dishes (Nunc, Roskilde, Denmark), precoated with 0.1% gelatin at a cell concentration of 2×10$^5$ cell/ml, in medium II containing DMEM F/12, 500 µg/ml insulin, 10,000 µg/ml transferrin, 0.63 µg/ml progesterone, 1.611 µg/ml putrascine, and 0.52 µg/ml of selenite with N2 and B27 supplement (both from Gibco), and 1 mM L-Glutamine and 10 ng/ml of bFGF (R&D systems). At this stage, the appearance of pancreatic islet-like clusters was monitored and assessed using immunochemistry with tissue-specific markers such as PDX-1.

To induce hepatocyte differentiation, 10 day-old EBs were plated onto 35 mm plastic tissue culture plates (Nunc) pre-coated with 1% matrigel (BD Biosciences, Bedford, Mass., USA) and allowed to differentiate for 25-30 days in the medium containing DMEM (high glucose), 10% FBS, L-glutamine (1 mM), non-essential amino acids (1%), β-mercaptoethanol (0.1 mM), hepatocyte growth factor (HGF) 20 ηg/ml, FGF4 (10 ηg/ml), human oncostatin (10 ηg/ml), insulin-transferrin-selenious acid (ITS) (1×), dexamethasone ($10^{-5}$ mM) and EGF (20 ηg/ml) (All the growth factors are from R&D Biosystems). During the period of differentiation, the cultures were monitored for appearance of oval shaped cells. For further characterization, 2-well chamber slides containing day-20 differentiated cells were analyzed.

The differentiation potential of the cell line into cells of multiple phenotypes was examined. EBs formed from the human ES cell colonies were induced into neuroectodermal, mesodermal and endodermal fate after attachment onto culture dishes. On the addition of ITSFn media, EBs started proliferating and developed multiple neurite-like extensions within a week. These neural precursors when cultured in N2 media on tissue culture plates pre-coated with poly-1-ornithine and laminin developed rounded cell bodies, which progressively assumed neuronal morphology, developing bipolar and multi-polar extensions that resulted in networks. Upon withdrawal of bFGF and addition of differentiation media, these cells exhibited a typical neuronal appearance with processes that continued to elaborate, displaying primary and secondary branches (FIG. 12.1). Indirect immunostaining showed that these cells were immunoreactive to the neuron-specific protein marker MAP-2 (FIG. 12.2). Since cell dimensions and orientations are key determinants of cardiac cell networks, the structural properties of human ES cell-derived cardiac colonies were studied. Spontaneously contracting areas were identified at the outgrowth of the EBs during the 15-18 days of differentiation (FIG. 12.3). Further, immunochemistry showed the presence of cardiac troponin-I (cTnI) (1:200, Chemicon, Temecula, Calif., USA), a cardiac specific protein that is involved in the regulation of cardiac muscle contraction in differentiated EBs (FIG. 12.4). After expansion of pancreatic progenitor cells, pancreatic islet-like clusters were observed, which was confirmed by immunostaining with the PDX-1 marker (FIGS. 12.5 and 12.6). After 15-18 days of differentiation, the cluster of oval-shaped cells seen was indicative of hepatocyte differentiation. AFP, an early endoderm-specific marker, was detected after 15-days of differentiation. Further, immunostaining using CK18 confirmed the presence of keratin, which is appropriate for hepatoblasts (FIGS. 12.7 and 12.8).

All of the compositions and methods disclosed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein to achieve the same or similar results. All such similar substitutes and modifications apparent to those skilled in the art are deemed to be within the spirit, scope and concept of the invention.

What is claimed is:

1. An isolated pluripotent human embryonic stem cell line deposited as ATCC Patent Deposit Designation No. PTA-8172.

2. A method of screening a substance for its effect on a purified preparation of pluripotent human embryonic stem cells, comprising:
   a) obtaining the purified preparation of pluripotent human embryonic stem cells;
   b) combining the preparation of pluripotent human embryonic stem cells with the substance; and
   c) determining any effect of the substance on the cells in the preparation;
   wherein the purified preparation of pluripotent human embryonic stem cells is from the pluripotent human embryonic stem cell line deposited as ATCC Patent Deposit Designation No. PTA-8172.

* * * * *

SEQUENCE LISTING

```
<160> NUMBER OF SEQ ID NOS: 60

<210> SEQ ID NO 1
<211> LENGTH: 26
<212> TYPE: DNA
<213> ORGANISM: Artificial Sequence
<220> FEATURE:
<223> OTHER INFORMATION: PCR Primer

<400> SEQUENCE: 1
tgaaggtcgg agtcaacgga tttggt                                          26

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
catgtgggcc atgaggtcca ccac                                            24

<210> SEQ ID NO 3
<211> LENGTH: 26
<212> TYPE: DNA
<213> ORGANISM: Artificial Sequence
<220> FEATURE:
<223> OTHER INFORMATION: PCR Primer

<400> SEQUENCE: 3
```

```
cgatgaagct ggagaaggag aagctg                                          26

<210> SEQ ID NO 4
<211> LENGTH: 25
<212> TYPE: DNA
<213> ORGANISM: Artificial Sequence
<220> FEATURE:
<223> OTHER INFORMATION: PCR Primer

<400> SEQUENCE: 4
caagggccgc agcttacaca tgttc                                           25

<210> SEQ ID NO 5
<211> LENGTH: 25
<212> TYPE: DNA
<213> ORGANISM: Artificial Sequence
<220> FEATURE:
<223> OTHER INFORMATION: PCR Primer

<400> SEQUENCE: 5
cctcctccat ggatctgctt attca                                           25

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
caggtcttca cctgtttgta gctgag                                          26

<210> SEQ ID NO 7
<211> LENGTH: 23
<212> TYPE: DNA
<213> ORGANISM: Artificial Sequence
<220> FEATURE:
<223> OTHER INFORMATION: PCR Primer

<400> SEQUENCE: 7
gcgtacgcaa attaaagtcc aga                                             23

<210> SEQ ID NO 8
<211> LENGTH: 25
<212> TYPE: DNA
<213> ORGANISM: Artificial Sequence
<220> FEATURE:
<223> OTHER INFORMATION: PCR Primer

<400> SEQUENCE: 8
cagcatccta aacagctcgc agaat                                           25

<210> SEQ ID NO 9
<211> LENGTH: 18
<212> TYPE: DNA
<213> ORGANISM: Artificial Sequence
<220> FEATURE:
<223> OTHER INFORMATION: PCR Primer

<400> SEQUENCE: 9
cccccggcgg caatagca                                                   18

<210> SEQ ID NO 10
<211> LENGTH: 20
<212> TYPE: DNA
<213> ORGANISM: Artificial Sequence
```

```
<220> FEATURE:
<223> OTHER INFORMATION: PCR Primer

<400> SEQUENCE: 10
tcggcgccgg ggagatacat                                              20

<210> SEQ ID NO 11
<211> LENGTH: 25
<212> TYPE: DNA
<213> ORGANISM: Artificial Sequence
<220> FEATURE:
<223> OTHER INFORMATION: PCR Primer

<400> SEQUENCE: 11
catgagaata ccagcagttc accca                                        25

<210> SEQ ID NO 12
<211> LENGTH: 25
<212> TYPE: DNA
<213> ORGANISM: Artificial Sequence
<220> FEATURE:
<223> OTHER INFORMATION: PCR Primer

<400> SEQUENCE: 12
cacttgacca gtttgtctct gagca                                        25

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
ctacaacgcc tacgagtcct aca                                          23

<210> SEQ ID NO 14
<211> LENGTH: 24
<212> TYPE: DNA
<213> ORGANISM: Artificial Sequence
<220> FEATURE:
<223> OTHER INFORMATION: PCR Primer

<400> SEQUENCE: 14
gttgcaccag aaaagtcaga gttg                                         24

<210> SEQ ID NO 15
<211> LENGTH: 21
<212> TYPE: DNA
<213> ORGANISM: Artificial Sequence
<220> FEATURE:
<223> OTHER INFORMATION: PCR Primer

<400> SEQUENCE: 15
gtttatccgt ggtgtgtctg g                                            21

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
ctgagctata gaggcctggg                                              20
```

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
atgggaactc tcccggcacg                                        20

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
tcacttcatc caagggccta                                        20

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
accagctgct gaccttgaac                                        20

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
ttgaacgtac ccaagaacga                                        20

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
acagaacctg ctgcctgaat                                        20

<210> SEQ ID NO 22
<211> LENGTH: 20
<212> TYPE: DNA
<213> ORGANISM: Artificial Sequence
<220> FEATURE:
<223> OTHER INFORMATION: PCR Primer

<400> SEQUENCE: 22
atcacagccg ggtagaaatg                                        20

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
agctatgccc ggacctctat                                                     20

<210> SEQ ID NO 24
<211> LENGTH: 20
<212> TYPE: DNA
<213> ORGANISM: Artificial Sequence
<220> FEATURE:
<223> OTHER INFORMATION: PCR Primer

<400> SEQUENCE: 24
gcctgcagca ggaggatctt                                                     20

<210> SEQ ID NO 25
<211> LENGTH: 23
<212> TYPE: DNA
<213> ORGANISM: Artificial Sequence
<220> FEATURE:
<223> OTHER INFORMATION: PCR Primer

<400> SEQUENCE: 25
taccatgcga ccagtggtgc gct                                                 23

<210> SEQ ID NO 26
<211> LENGTH: 23
<212> TYPE: DNA
<213> ORGANISM: Artificial Sequence
<220> FEATURE:
<223> OTHER INFORMATION: PCR Primer

<400> SEQUENCE: 26
gaattctggt tatcatcggg gaa                                                 23

<210> SEQ ID NO 27
<211> LENGTH: 24
<212> TYPE: DNA
<213> ORGANISM: Artificial Sequence
<220> FEATURE:
<223> OTHER INFORMATION: PCR Primer

<400> SEQUENCE: 27
ctatgcaatg cgctggaaac aaca                                                24

<210> SEQ ID NO 28
<211> LENGTH: 21
<212> TYPE: DNA
<213> ORGANISM: Artificial Sequence
<220> FEATURE:
<223> OTHER INFORMATION: PCR Primer

<400> SEQUENCE: 28
ccctgatttg ctactggcag t                                                   21

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
tgaggtcaag gcacagtacg                                                     20

<210> SEQ ID NO 30

```
<211> LENGTH: 20
<212> TYPE: DNA
<213> ORGANISM: Artificial Sequence
<220> FEATURE:
<223> OTHER INFORMATION: PCR Primer

<400> SEQUENCE: 30
tgatgttccg gttcatctca                                              20

<210> SEQ ID NO 31
<211> LENGTH: 20
<212> TYPE: DNA
<213> ORGANISM: Artificial Sequence
<220> FEATURE:
<223> OTHER INFORMATION: PCR Primer

<400> SEQUENCE: 31
cacagtctgc tgaggttgga                                              20

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
gagctgctcc atctgtaggg                                              20

<210> SEQ ID NO 33
<211> LENGTH: 20
<212> TYPE: DNA
<213> ORGANISM: Artificial Sequence
<220> FEATURE:
<223> OTHER INFORMATION: PCR Primer

<400> SEQUENCE: 33
ggaggtggaa gccgaagtat                                              20

<210> SEQ ID NO 34
<211> LENGTH: 20
<212> TYPE: DNA
<213> ORGANISM: Artificial Sequence
<220> FEATURE:
<223> OTHER INFORMATION: PCR Primer

<400> SEQUENCE: 34
gagaggagac caccatcgcc                                              20

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
tacagcccca tctccaactc                                              20

<210> SEQ ID NO 36
<211> LENGTH: 20
<212> TYPE: DNA
<213> ORGANISM: Artificial Sequence
<220> FEATURE:
<223> OTHER INFORMATION: PCR Primer

<400> SEQUENCE: 36
```
gctccgactt caccagagag				20

<210> SEQ ID NO 37
<211> LENGTH: 24
<212> TYPE: DNA
<213> ORGANISM: Artificial Sequence
<220> FEATURE:
<223> OTHER INFORMATION: PCR Primer

<400> SEQUENCE: 37
tgaacacaga cgctatgcgc tcag			24

<210> SEQ ID NO 38
<211> LENGTH: 25
<212> TYPE: DNA
<213> ORGANISM: Artificial Sequence
<220> FEATURE:
<223> OTHER INFORMATION: PCR Primer

<400> SEQUENCE: 38
cacctttatg tgagtggaca cagag			25

<210> SEQ ID NO 39
<211> LENGTH: 21
<212> TYPE: DNA
<213> ORGANISM: Artificial Sequence
<220> FEATURE:
<223> OTHER INFORMATION: PCR Primer

<400> SEQUENCE: 39
taaggtggat cttcaggtag c				21

<210> SEQ ID NO 40
<211> LENGTH: 21
<212> TYPE: DNA
<213> ORGANISM: Artificial Sequence
<220> FEATURE:
<223> OTHER INFORMATION: PCR Primer

<400> SEQUENCE: 40
catctcattg gtgagctccc t				21

<210> SEQ ID NO 41
<211> LENGTH: 20
<212> TYPE: DNA
<213> ORGANISM: Artificial Sequence
<220> FEATURE:
<223> OTHER INFORMATION: PCR Primer

<400> SEQUENCE: 41
gtcgagccta gactgcctgt				20

<210> SEQ ID NO 42
<211> LENGTH: 20
<212> TYPE: DNA
<213> ORGANISM: Artificial Sequence
<220> FEATURE:
<223> OTHER INFORMATION: PCR Primer

<400> SEQUENCE: 42
ggtatatcgg gttggggttc				20

<210> SEQ ID NO 43
<211> LENGTH: 21
<212> TYPE: DNA

<210> SEQ ID NO 44
<211> LENGTH: 20
<212> TYPE: DNA
<213> ORGANISM: Artificial Sequence
<220> FEATURE:
<223> OTHER INFORMATION: PCR Primer

<400> SEQUENCE: 43
ccttcccttt aaccctcaca c                                              21

<210> SEQ ID NO 44
<211> LENGTH: 20
<212> TYPE: DNA
<213> ORGANISM: Artificial Sequence
<220> FEATURE:
<223> OTHER INFORMATION: PCR Primer

<400> SEQUENCE: 44
ccgatttctc tgcgcttttc                                                20

<210> SEQ ID NO 45
<211> LENGTH: 23
<212> TYPE: DNA
<213> ORGANISM: Artificial Sequence
<220> FEATURE:
<223> OTHER INFORMATION: PCR Primer

<400> SEQUENCE: 45
gcctagccac cactgcgctt ttc                                            23

<210> SEQ ID NO 46
<211> LENGTH: 20
<212> TYPE: DNA
<213> ORGANISM: Artificial Sequence
<220> FEATURE:
<223> OTHER INFORMATION: PCR Primer

<400> SEQUENCE: 46
cggctcactg gtttaactcc                                                20

<210> SEQ ID NO 47
<211> LENGTH: 20
<212> TYPE: DNA
<213> ORGANISM: Artificial Sequence
<220> FEATURE:
<223> OTHER INFORMATION: PCR Primer

<400> SEQUENCE: 47
tctatgaggg ctacgctttg                                                20

<210> SEQ ID NO 48
<211> LENGTH: 20
<212> TYPE: DNA
<213> ORGANISM: Artificial Sequence
<220> FEATURE:
<223> OTHER INFORMATION: PCR Primer

<400> SEQUENCE: 48
cctgactgga aggtagatgg                                                20

<210> SEQ ID NO 49
<211> LENGTH: 20
<212> TYPE: DNA
<213> ORGANISM: Artificial Sequence
<220> FEATURE:
<223> OTHER INFORMATION: PCR Primer

<400> SEQUENCE: 49
agaacctgtc acaagctgtg                                                20

```
<210> SEQ ID NO 50
<211> LENGTH: 20
<212> TYPE: DNA
<213> ORGANISM: Artificial Sequence
<220> FEATURE:
<223> OTHER INFORMATION: PCR Primer

<400> SEQUENCE: 50
gacagcaagc tgaggatgtc                                              20

<210> SEQ ID NO 51
<211> LENGTH: 20
<212> TYPE: DNA
<213> ORGANISM: Artificial Sequence
<220> FEATURE:
<223> OTHER INFORMATION: PCR Primer

<400> SEQUENCE: 51
ctccttcagg cagtgagagc                                              20

<210> SEQ ID NO 52
<211> LENGTH: 20
<212> TYPE: DNA
<213> ORGANISM: Artificial Sequence
<220> FEATURE:
<223> OTHER INFORMATION: PCR Primer

<400> SEQUENCE: 52
gagatgcagt gtgctcgtgc                                              20

<210> SEQ ID NO 53
<211> LENGTH: 20
<212> TYPE: DNA
<213> ORGANISM: Artificial Sequence
<220> FEATURE:
<223> OTHER INFORMATION: PCR Primer

<400> SEQUENCE: 53
tctcatgttg aagccactgc                                              20

<210> SEQ ID NO 54
<211> LENGTH: 19
<212> TYPE: DNA
<213> ORGANISM: Artificial Sequence
<220> FEATURE:
<223> OTHER INFORMATION: PCR Primer

<400> SEQUENCE: 54
ggtttgtttc tcgggttga                                               19

<210> SEQ ID NO 55
<211> LENGTH: 20
<212> TYPE: DNA
<213> ORGANISM: Artificial Sequence
<220> FEATURE:
<223> OTHER INFORMATION: PCR Primer

<400> SEQUENCE: 55
gacaagtgag agagcaagtg                                              20

<210> SEQ ID NO 56
<211> LENGTH: 19
<212> TYPE: DNA
<213> ORGANISM: Artificial Sequence
<220> FEATURE:
```

```
<223> OTHER INFORMATION: PCR Primer

<400> SEQUENCE: 56
acagtagtgg aaaccggag                                                    19

<210> SEQ ID NO 57
<211> LENGTH: 26
<212> TYPE: DNA
<213> ORGANISM: Artificial Sequence
<220> FEATURE:
<223> OTHER INFORMATION: PCR Primer

<400> SEQUENCE: 57
cctttggcac aatgaagtgg gtaacc                                            26

<210> SEQ ID NO 58
<211> LENGTH: 25
<212> TYPE: DNA
<213> ORGANISM: Artificial Sequence
<220> FEATURE:
<223> OTHER INFORMATION: PCR Primer

<400> SEQUENCE: 58
cagcagtcag ccatttcacc atagg                                             25

<210> SEQ ID NO 59
<211> LENGTH: 18
<212> TYPE: DNA
<213> ORGANISM: Artificial Sequence
<220> FEATURE:
<223> OTHER INFORMATION: PCR Primer

<400> SEQUENCE: 59
gtcctggagg agcccaac                                                     18

<210> SEQ ID NO 60
<211> LENGTH: 18
<212> TYPE: DNA
<213> ORGANISM: Artificial Sequence
<220> FEATURE:
<223> OTHER INFORMATION: PCR Primer

<400> SEQUENCE: 60
gcagtcctgc tcaggctc                                                     18
```